(12) United States Patent
Medema et al.

(10) Patent No.: US 9,000,128 B2
(45) Date of Patent: Apr. 7, 2015

(54) ANTIBODIES AGAINST A PROLIFERATING INDUCING LIGAND (APRIL) AND METHODS OF USE THEREOF

(71) Applicants: Jan Paul Medema, Amsterdam (NL); Hans Van Eenennaam, Oss (NL); Marco Guadagnoli, Amsterdam (NL); Fiona Clare Kimberley, Amsterdam (NL); Uyen Truong Phan, Palo Alto, CA (US)

(72) Inventors: Jan Paul Medema, Amsterdam (NL); Hans Van Eenennaam, Oss (NL); Marco Guadagnoli, Amsterdam (NL); Fiona Clare Kimberley, Amsterdam (NL); Uyen Truong Phan, Palo Alto, CA (US)

(73) Assignee: Bionovion Holding B.V., Oss (NL)

( * ) Notice: Subject to any disclaimer, the term of this patent is extended or adjusted under 35 U.S.C. 154(b) by 0 days.

(21) Appl. No.: 13/792,339

(22) Filed: Mar. 11, 2013

(65) Prior Publication Data

US 2013/0273064 A1    Oct. 17, 2013

Related U.S. Application Data

(60) Division of application No. 13/216,751, filed on Aug. 24, 2011, now Pat. No. 8,895,705, which is a continuation-in-part of application No. PCT/EP2010/052254, filed on Feb. 23, 2010.

(30) Foreign Application Priority Data

Mar. 2, 2009 (EP) .................................. 09154079
Apr. 9, 2009 (EP) .................................. 09157722

(51) Int. Cl.
*C07K 16/00* (2006.01)
*C12P 21/08* (2006.01)
*A61K 39/395* (2006.01)
*G01N 33/53* (2006.01)
*C07K 16/28* (2006.01)
*C07K 16/24* (2006.01)
*G01N 33/68* (2006.01)
*A61K 39/00* (2006.01)

(52) U.S. Cl.
CPC ......... *C07K 16/2878* (2013.01); *C07K 16/2875* (2013.01); *C07K 16/241* (2013.01); *G01N 33/6863* (2013.01); *A61K 2039/505* (2013.01); *C07K 2316/96* (2013.01); *C07K 2317/73* (2013.01); *C07K 2317/92* (2013.01); *C07K 2319/30* (2013.01); *C07K 2319/32* (2013.01); *C07K 2317/34* (2013.01)

(58) Field of Classification Search
CPC ............. C07K 16/241; A61K 39/3955; A61K 2039/505
See application file for complete search history.

(56) References Cited

FOREIGN PATENT DOCUMENTS

WO    WO 01/60397    * 8/2001
WO    WO 02/094192    * 11/2002

OTHER PUBLICATIONS

Colman, PM. Research in Immunology, Elsevier, NY, 145(1):33-36, 1994.*
Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*

* cited by examiner

*Primary Examiner* — Robert Landsman
(74) *Attorney, Agent, or Firm* — Vedder Price PC; Thomas J. Kowalski; Deborah L. Lu

(57) ABSTRACT

The present invention relates to a binding compound which binds to human APRIL. More specifically the invention provides, compositions of anti-APRIL specific antibodies and methods to use such antibodies in modulating the biological activity APRIL, particularly in inflammatory diseases, inhibition of cell proliferation and cancer.

14 Claims, 10 Drawing Sheets

A.

B.

A. Anti-FLAG Ab +FLAG-hAPRIL

B. BCMA-Fc + FLAG-hAPRIL

C. Blocking FLAG-hAPRIL to BCMA-Fc

D. Blocking FLAG-hAPRIL to TACI-Fc

A.

B.

Figure 4. A
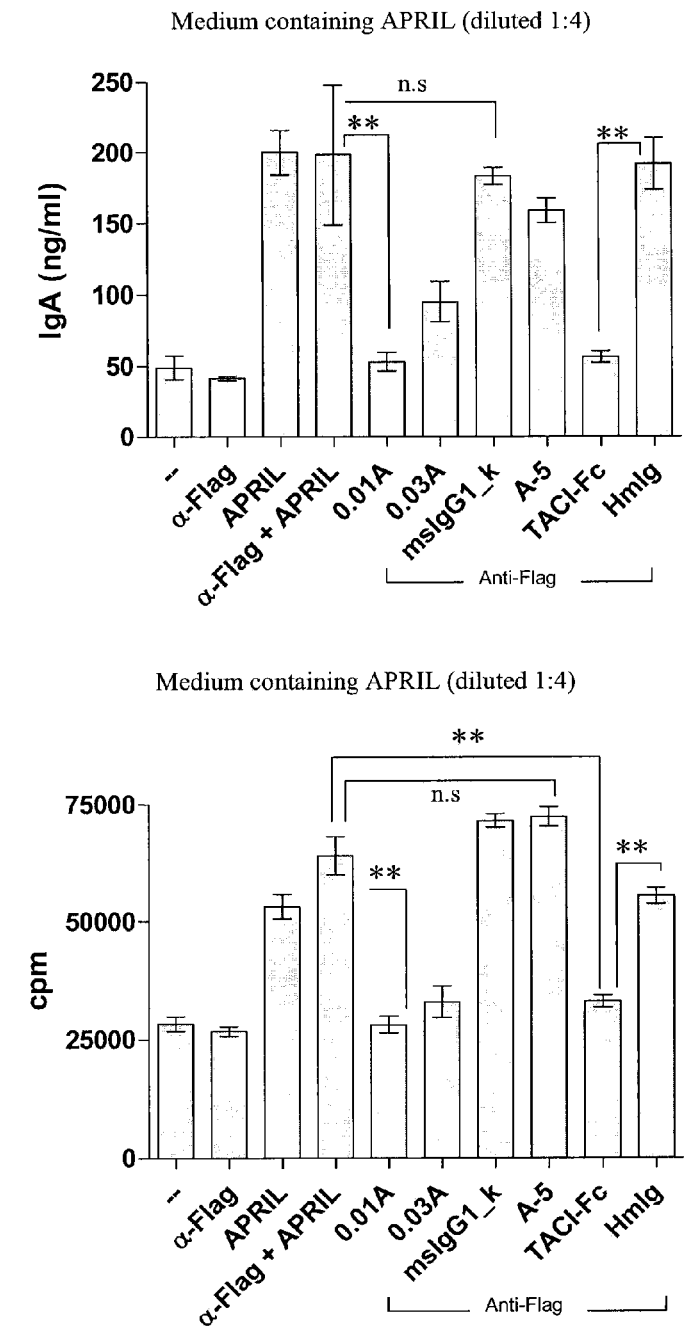

Figure 4. B
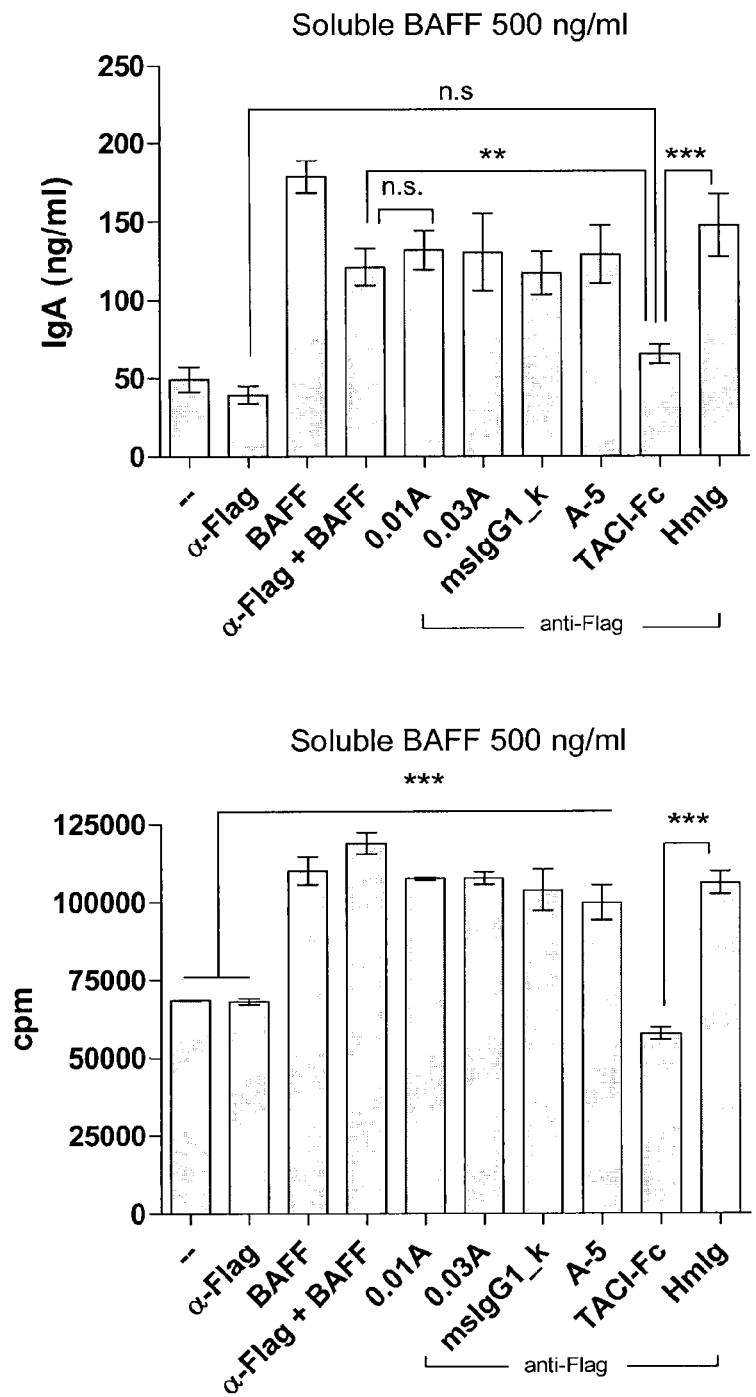

Figure 5. A
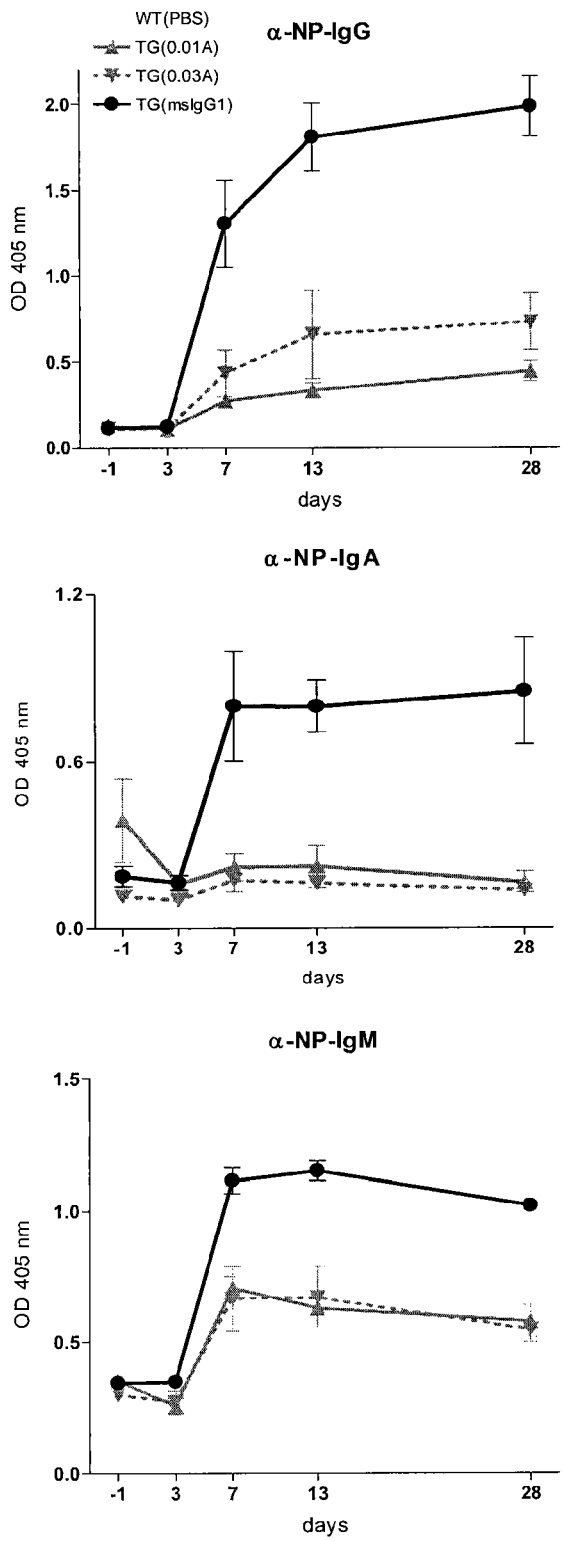

Figure 5. B
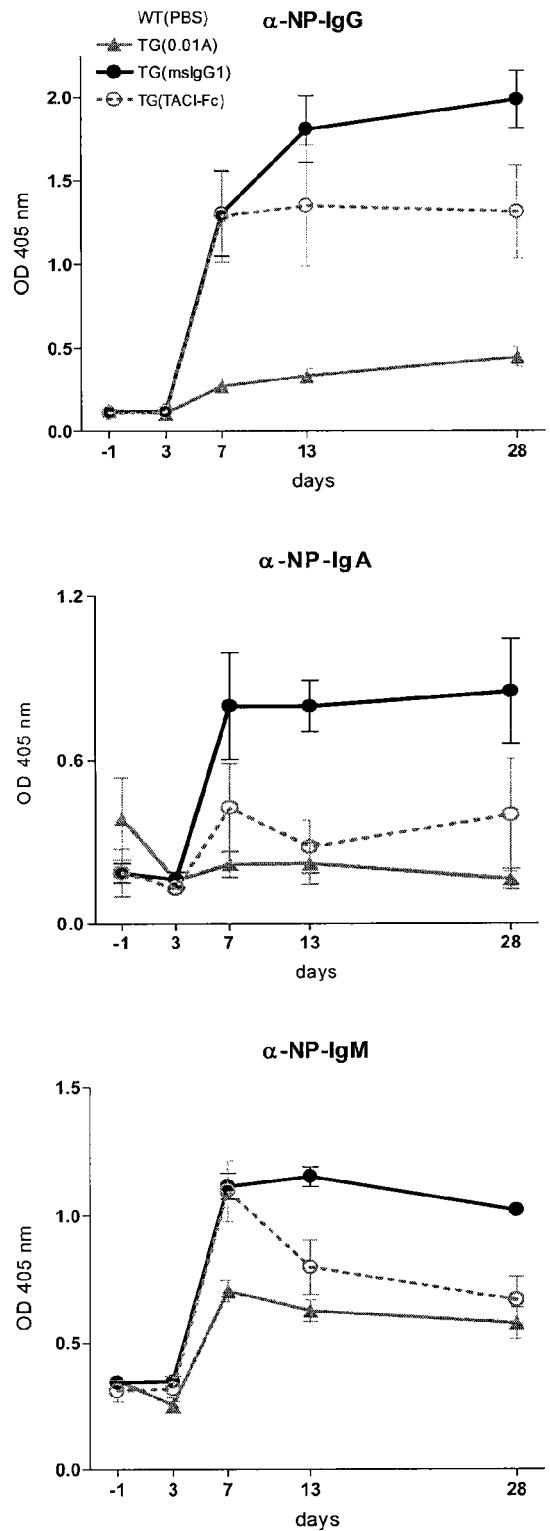

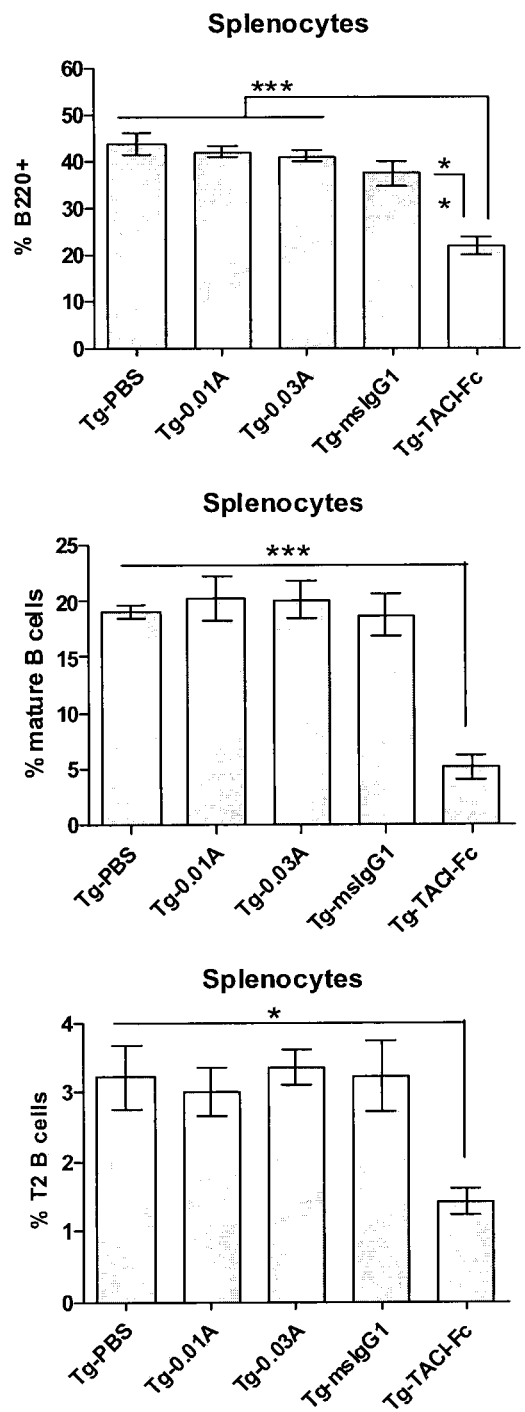
Figure 6. A

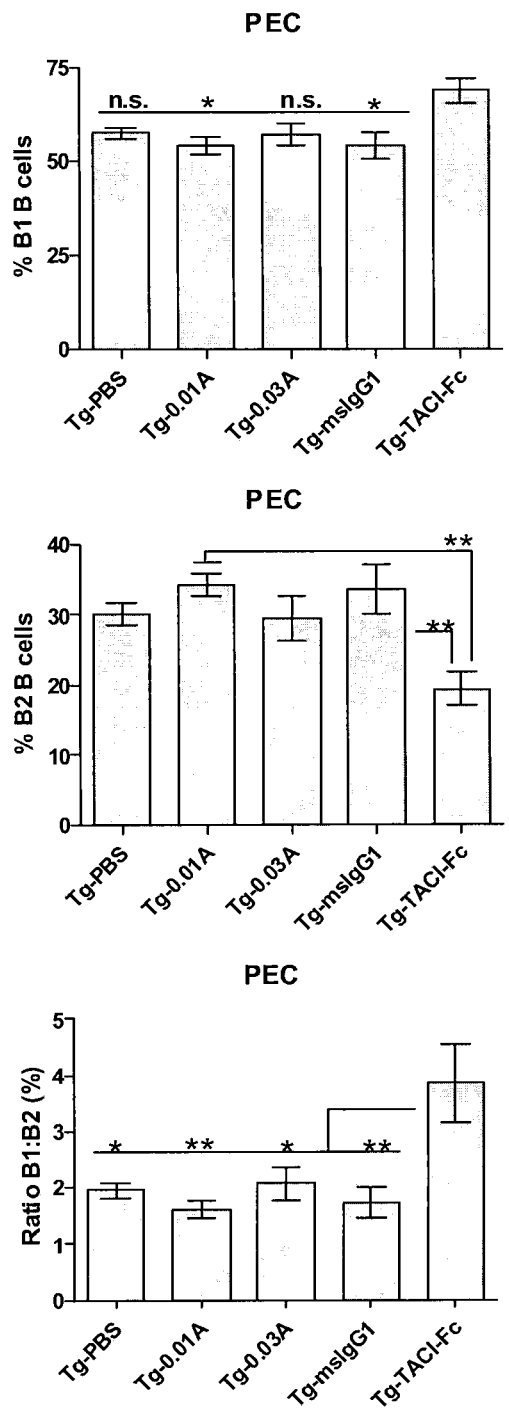
Figure 6. B

Figure 7.

A.
hAPRIL.01A Heavy Chain

```
<-----------FWR1-------------->  <CDR1>  <----FWR2---->   <------CDR2----->
EVQLQQSGPELVKPGASVKMSCKASGYTFT   SYVMH   WVKQKPGQGLEWIG   YINPYNDAPKYNEKFKG

<------------FWR3-------------->  <---CDR3--->   <---FWR4-->
KATVTSDKSSGTAYMELSSLTSEDSAVYYCAR  GLGYALYYAMDY   WGQGTSVTVSS
```

B.
hAPRIL.01A Light Chain

```
<--------FWR1--------->   <---CDR1-->   <-----FWR2---->   <-CDR2->
DIVMTQSQKFKSTSVGDRVSVTC   KASQNVGNNVA   WYQQKAGQSPKALIS   SASNRDS

<-------------FWR3------------->  <--CDR3->   <---FWR4-->
GVPDRFTGSGSGTDFTLTISNVQSEDLADYFC  QQYNIYPFT   FGSGTELEIK
```

C.
hAPRIL.03A Heavy Chain

```
<-----------FWR1-------------->  <-CDR1->  <----FWR2---->   <-----CDR2----->
QVTLKESGPGILQPSQTLSLTCSFSGFSLS   TYGIGVG   WIRQPSGKGLEWLA   HIWWNDNKYYNTALKS

<-------------FWR3-------------->  <---CDR3--->   <---FWR4-->
RLTISKDTSNNQVFLKIASVDTADTATYYCAR   IAGGNYDYAMDH   WGQGTSVTVSS
```

D.
hAPRIL.03A Light Chain

```
<--------FWR1--------->   <---CDR1--->   <-----FWR2---->   <-CDR2->
QIVLTQSPAIMSTSPGEKVTLTC   SASSSVSSTYLY   WYQQKPGSSPKLWIY   STSNLAS

<------------FWR3-------------->  <--CDR3->   <---FWR4-->
GVPARFSGSGSGTSYSLTISSMEAEDAASYFC  HQWSSYPPT   FGAGTKLELK
```

US 9,000,128 B2

ANTIBODIES AGAINST A PROLIFERATING INDUCING LIGAND (APRIL) AND METHODS OF USE THEREOF

INCORPORATION BY REFERENCE

This application is a divisional of patent application Ser. No. 13/216,751 filed Aug. 24, 2011 which claims priority to international patent application Serial No. PCT/EP2010/052254 filed Feb. 23, 2010.

This application is a divisional application of U.S. patent application Ser. No. 13/216,751, filed Aug. 24, 2011, now U.S. Pat. No. 8,895,705 issued Nov. 25, 2014, which is a continuation-in-part application of international patent application Serial No. PCT/EP2010/052254, filed Feb. 23, 2010, which published as PCT Publication No. WO 2010/100056 on Sep. 10, 2010, which claims benefit of European patent application Serial Nos. 09154079.9, filed Mar. 2, 2009 and 09157722.1, filed Apr. 9, 2009.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference, and may be employed in the practice of the invention.

FIELD OF THE INVENTION

The present invention relates to isolated antibodies or fragments thereof which binds to human A PRoliferating Inducing Ligand (APRIL), polynucleotides encoding such antibodies and host cells producing said antibodies. The antibodies can be used to inhibit immune cell proliferation and/or survival, to treat cancer and to treat an inflammatory disease.

BACKGROUND OF THE INVENTION

APRIL is expressed as a type-II transmembrane protein, but unlike most other TNF family members it is mainly processed as a secreted protein and cleaved in the Golgi apparatus where it is cleaved by a furin convertase to release a soluble active form (Lopez-Fraga et al., 2001, *EMBO Rep* 2, 945-51). APRIL assembles as a non-covalently linked homotrimer with similar structural homology in protein fold to a number of other TNF family ligands (Wallweber et al., 2004, *Mol Biol* 343, 283-90). APRIL binds two TNF receptors: B cell maturation antigen (BCMA) and transmembrane activator and calcium modulator and cyclophilin ligand interactor (TACI) (reviewed in Kimberley et al., 2009, *J Cell Physiol.* 218 (1):1-8). In addition, APRIL has recently been shown to bind heparan sulphate proteoglycans (HSPGs) (Hendriks et al., 2005, *Cell Death Differ* 12, 637-48).

APRIL shows high homology (30%) to another member of the TNF superfamily, B cell activating factor belonging to the TNF family (BAFF or B Lymphocyte stimulator, BLyS), with which it shares binding to its receptors, BCMA and TACI. BAFF is also known to bind a unique receptor, BAFF-Receptor, and through this mediates crucial survival signals during B cell development (reviewed in Kimberley et al., 2009, *J Cell Physiol.* 218 (1):1-8). APRIL and BAFF have been suggested to form mixed trimers (Roschke et al., 2002, *J Immunol.* 169 (8):4314-21). Such mixed trimers were found to occur at a higher prevalence in rheumatoid arthritis (RA) patients.

APRIL is predominantly expressed by immune cell subsets such as monocytes, macrophages, dendritic cells, neutrophils, B-cells, and T-cells, many of which also express BAFF. In addition, APRIL can be expressed by non-immune cells such as osteoclasts, epithelial cells and a variety of tumour tissues (reviewed in Kimberley et al., 2009, *J Cell Physiol.* 218 (1):1-8).

The function of APRIL was established using mouse genetic models. hAPRIL transgenic mice develop normally, but showed enhanced T cell survival and elevated levels of IgM antibodies (Stein et al., 2002, *J Clin Invest* 109, 1587-98). In addition, T cell independent type II responses were enhanced. Aged hAPRIL transgenic mice displayed extreme enlargement and re-organisation of the lymph system and enlarged spleen due to infiltration of CD5 positive B cells, a phenotype closely resembling human B-CLL (Planelles et al., 2004, *Cancer Cell* 6, 399-408). APRIL deficient mice were found to have decreased levels of IgA in circulation and upon challenge with a T-cell dependent antigen (Castigli et al., 2004, *Proc Natl Acad Sci USA* 101, 3903-8; Varfolomeev et al., 2004, *Mol Cell Biol* 24, 997-1006). Next, APRIL, along with BAFF, was demonstrated to function in class-switch recombination (CSR) of antibodies to both IgG and IgA, independently of CD40CD40L signaling (Litinskiy et al., 2002, *Nat Immunol* 3, 822-9). In addition, APRIL was demonstrated to be less critical than BAFF in B cell maintenance, but was shown to have a role in B cell signalling and drive both proliferation and survival of human and murine B cells in-vitro (reviewed in Kimberley et al., 2009, *J Cell Physiol.* 218 (1):1-8).

APRIL was originally identified based on its expression in cancer cells (Hahne et al., 1998, *J Exp Med* 188, 1185-90). High expression levels of APRIL mRNA were found in a panel of tumour cell lines as well as human primary tumours such as colon, and a lymphoid carcinoma. In addition, APRIL transfected murine fibroblast NIH-3T3 cells were shown to grow more rapidly in immunodeficient mice. More importantly, blocking APRIL using a soluble APRIL receptor was shown to inhibit tumour growth of lung and colon carcinomas (Rennert et al., 2000, *J Exp Med* 192, 1677-84).

Chronic Lymphocytic Leukaemia (CLL) B cells express both APRIL and APRIL-receptors. In addition, it was shown that APRIL protected CLL cells against spontaneous and drug-induced apoptosis and stimulated NF-κB activation (reviewed in Kimberley et al., 2009, *J Cell Physiol.* 218 (1):1-8). A retrospective study under 95 CLL patients showed increased levels of APRIL in serum, which correlated with disease progression and overall patient survival, with a poorer prognosis for patients with high APRIL serum levels (Planelles et al., 2007, *Haematologica* 92, 1284-5).

Similarly, (increased levels of) APRIL was shown to be expressed in Hodgkin's lymphoma, Non-Hodgkin's lymphoma (NHL) and Multiple Myeloma (MM) (reviewed in Kimberley et al., 2009, *J Cell Physiol.* 218 (1):1-8). A retrospective study in DLBCL patients (NHL) showed that high APRIL expression in cancer lesions correlated with a poor survival rate (Schwaller et al., 2007, *Blood* 109, 331-8). Using NHL and MM cell-lines it was shown that treatment with APRIL or BAFF increased survival via NF-κB activation and up-regulation of pro-survival proteins (reviewed in Kimberley et al., 2009, *J Cell Physiol.* 218 (1):1-8). In accordance with this pro-survival role of APRIL, MM cells were shown to undergo apoptosis when cultured in the presence of TACI-Fc. Since BAFF-receptor was less effective in enhancing apoptosis, this indicates that APRIL, and not BAFF is primarily responsible for enhanced survival in these cells (Abe et al., 2006, *Leukemia* 20, 1313-5).

APRIL was also found to be over-expressed in a number of cell lines derived from solid tumours. Indeed, APRIL was able to stimulate in-vitro proliferation of a number of these cell lines (reviewed in Kimberley et al., 2009, *J Cell Physiol.* 218 (1):1-8).

Due to its role in B cell biology APRIL also plays a role in many autoimmune diseases. Indeed, atacicept (a commercial TACI-Fc preparation) is already in numerous clinical trials for treatment of several autoimmune diseases (reviewed in Gatto et al., 2008, *Curr Opin Investig Drugs.* 9 (11):1216-27). Increased serum levels of APRIL and BAFF have been reported in many SLE patients (Koyama et al., 2005, *Ann Rheum Dis* 64, 1065-7). A retrospective analysis revealed that APRIL serum levels tended to correlate with anti-dsDNA antibody titres. Evidence that APRIL may play a functional role in SLE was obtained by testing the effect of TACI-Fc fusion protein into lupus prone mice (Gross et al., 2000, *Nature* 404, 995-9), which prevented disease development and prolonged survival.

In addition, inhibition of APRIL and BAFF with TACI-Fc in the CIA mouse model of rheumatoid arthritis was also found to prevent disease progression and lower disease scores, compared with controls (Gross et al., 2001, *Immunity* 15, 289-302; Wang et al., 2001, *Nat Immunol* 2, 632-7). Also in another arthritis model, synovium-SCID mouse chimeras, TACI-Fc showed a beneficial effect (Seyler et al., 2005, *J Clin Invest* 115, 3083-92). Treatment with TACI-Fc resulted in the disappearance of Germinal Centers in the synovial tissue, decreased Ig production and decreased production of IFN-gamma.

It was later reported that the synovial fluid of patients with inflammatory arthritis had significantly increased APRIL levels compared with those with patients suffering from non-inflammatory arthritis such as osteoarthritis (Stohl et al., 2006, *Endocr Metab Immune Disord Drug Targets* 6, 351-8; Tan et al., 2003, *Arthritis Rheum* 48, 982-92).

Several studies focused on the presence of APRIL in the sera of patients suffering from a wider range of systemic immune-based rheumatic diseases (now also including Sjögren's syndrome, Reiter's syndrome, psoriatic arthritis, polymyositis, and ankylosing spondylitis) and found significantly increased APRIL levels in these patients, suggesting an important role for APRIL in these diseases as well (Jonsson et al., 1986, *Scand J Rheumatol Suppl* 61, 166-9; Roschke et al., 2002, *J Immunol* 169, 4314-21).

Finally, increased APRIL expression has also been linked to Multiple Sclerosis (MS). APRIL expression was found to be increased in the astrocytes of MS sufferers compared with normal controls. This is in line with the described APRIL expression in glioblastomas and in the serum of glioblastoma patients (Deshayes et al., 2004, *Oncogene* 23, 3005-12; Roth et al., 2001, *Cell Death Differ* 8, 403-10).

SUMMARY OF THE INVENTION

APRIL plays a crucial role in the survival and proliferative capacity of several B-cell malignancies, and potentially also some solid tumours. APRIL is also emerging as a key player in inflammatory diseases or autoimmunity. Thus, strategies to antagonise APRIL are a therapeutic goal for a number of these diseases. Indeed clinical studies targeting APRIL with TACI-Fc (Atacicept) are currently ongoing for treatment of several autoimmune diseases. However, TACI-Fc also targets BAFF, a factor involved in normal B-cell maintenance. Antibodies directed against APRIL have been described in WO9614328, WO2001/60397, WO2002/94192, WO9912965, WO2001/196528 and WO9900518. This invention describes antibodies targeting APRIL specifically. The antibodies in this invention fully block the binding of APRIL to TACI and at least partially to BCMA. Some antibodies according to the invention fully block the binding to both BCMA and TACI. Such molecules are useful in a therapy for a number of conditions in which circulating soluble APRIL correlates with disease activity and progression. Since expression levels of APRIL can be used as diagnostic and prognostic markers for different diseases, these antibodies can also be applied in such tests.

The invention provides binding compounds which include but are not limited to compounds such as isolated antibodies or antibody fragments which bind to human APRIL.

In some embodiments the binding compound blocks binding to TACI and BCMA. In some embodiments, the APRIL binding compound of the invention includes one or more of the antibody CDRs (Complementary Determining Regions) selected from SEQ ID NOs: 9, 10, 11, 12, 13, 14, 15, 16, 17, 18, 19 and 20; and in further embodiments, includes one or more antibody light chain CDRs of SEQ ID NOs: 12, 13, 14, 18, 19 and 20 and/or antibody heavy chain CDRs of SEQ ID NOs: 9, 10, 11, 15, 16 and 17. In some embodiments, the binding compound is a chimeric antibody, human antibody, humanized antibody or a fragment thereof.

In one embodiment, the invention provides a binding compound which bind to human APRIL comprising antibody heavy chain CDRs SEQ ID NOs: 9, 10 and 11, or variants of any said sequences; and antibody light chain CDRs SEQ ID NOs: 12, 13 and 14, or variants of any said sequences.

In another embodiment, the invention provides a binding compound which bind to human APRIL comprising antibody heavy chain CDRs SEQ ID NOs: 15, 16 and 17 or variants of any said sequences; and antibody light chain CDRs SEQ ID NOs: 18, 19 and 20 or variants of any said sequences.

In another embodiment, the invention comprises a binding compound which bind to human APRIL comprising an antibody heavy chain variable region comprising the amino acid sequence of SEQ ID NO: 5 and a antibody light chain variable region comprising the amino acid sequence selected from the group of SEQ ID NO: 6.

In yet another embodiment, the invention comprises a binding compound which bind to human APRIL comprising a antibody heavy chain variable region comprising the amino acid sequence of SEQ ID NO: 7 and a antibody light chain variable region comprising the amino acid sequence of SEQ ID NO: 8.

In another embodiment the invention comprises an antibody, wherein the heavy chain has the variable region sequence of SEQ ID NO: 5 and is joined to a IgG1 constant region and the light chain has the sequence of SEQ ID NO: 6 and is joined to the κ constant region. In particular, the constant region is from mouse or human origin. More in particular, the antibody is hAPRIL.01A.

In another embodiment the invention comprises an antibody, wherein the heavy chain has the variable region sequence of SEQ ID NO: 7 and is joined to a IgG1 constant region and the light chain has the sequence of SEQ ID NO: 8 and is joined to the κ constant region. In particular, the constant region is from mouse or human origin. More in particular, the antibody is hAPRIL.03A.

In another embodiment the invention comprises a variant of a binding compound which bind to human APRIL, wherein any of said variant(s) may comprise up to three amino acid modifications in the previous identified CDRs of each the antibody heavy and light chain variable regions.

In another embodiment the invention comprises a variant of a binding compound which binds to human APRIL, wherein any of said variant(s) may comprise up to three amino acid modifications in each of the previous identified CDRs in each of the antibody heavy and light chain variable regions.

In another embodiment the invention comprises a variant of a binding compound which binds to human APRIL, wherein any of said variant(s) may comprise up to three amino acid modifications in the previous identified CDR sequences in each of the antibody heavy and light chain variable regions.

The invention also comprises a binding compound that fully blocks the binding of APRIL with human TACI and at least partially blocks the binding with human BCMA.

In another embodiment the invention comprises a binding compound that fully blocks the binding of APRIL with human TACI and with human BCMA.

In another embodiment the invention comprises a binding compound which bind to human APRIL, wherein the binding compound binds human APRIL with a $K_D$ of about 10 nM or lower; and blocks binding of human TACI and/or human BCMA to human APRIL with an $IC_{50}$ of about 2 nM or lower.

The invention also comprises a binding compound which binds to human APRIL wherein the binding compound has the same epitope specificity as the antibodies described above i.e. competes for the binding epitope of the antibodies described above.

In some embodiments the invention comprises a binding compound which competes for a binding epitope on human APRIL with any of the antibodies described above, and binds human APRIL with a $K_D$ of about 10 nM or lower. In particular, the epitope on human APRIL is the epitope which bind to the antibodies hAPRIL.01A and hAPRIL.03A, preferably hAPRIL.01A.

In another embodiment the invention comprises a binding compound which competes for a binding epitope on human APRIL with any of the antibodies described above and binds to human APRIL with about the same $K_D$ as an antibody having a heavy chain comprising the amino acid sequence of SEQ ID NO: 5 and a light chain comprising the amino acid sequence of SEQ ID NO: 6.

In another embodiment the invention comprises a binding compound which competes for a binding epitope on human APRIL with any of the compounds described above and binds to human APRIL with about the same $K_D$ as an antibody having a heavy chain comprising the amino acid sequence of SEQ ID NO: 7 and a light chain comprising the amino acid sequence of SEQ ID NO: 8.

In another embodiment the invention comprises a binding compound which competes for a binding epitope on human APRIL with any of the antibodies described above and blocks binding of human TACI and/or human BCMA to human APRIL with an $IC_{50}$ of about 2 nM or lower.

In another embodiment the invention comprises a binding compound which binds to the conformational human APRIL epitope SMPSHP (SEQ ID NO: 34) (preferably IRSMPSHPDRA (SEQ ID NO: 33)) optionally supported by TLFR (SEQ ID NO: 35) and/or QDVTFTMGQ (SEQ ID NO: 36).

In yet another embodiment the invention comprises a binding compound which binds to the conformational human APRIL epitope VSREGQGRQ (SEQ ID NO: 38) optionally supported by TFTMGQ (SEQ ID NO: 39).

In some embodiments the binding compound of the invention is a chimeric antibody or a fragment thereof.

In another embodiment the binding compound of the invention is a human antibody or a fragment thereof.

In another embodiment the binding compound of the invention is a humanized antibody or a fragment thereof.

In another embodiment the invention comprises a binding compound, preferably a humanized antibody, with the above identified CDR's and a human heavy chain constant region variant and a human light chain constant region variant, wherein each constant region variant comprises up to 20 conservatively modified amino acid substitutions.

In another embodiment the binding compound of the invention is an antibody fragment selected from Fab, Fab', Fab'-SH, Fv, scFv, F(ab')$_2$, bispecific mAb or a diabody fragment.

The invention also comprises the binding compound as described above which inhibits the proliferation and survival of B-cells.

The invention also comprises nucleic acids encoding the anti-APRIL binding compound of the invention. Included in the invention are nucleic acids encoding any one of the amino acid sequences enclosed in SEQ ID NOS: 5 to 20. Also included within the invention are nucleic acids comprising SEQ ID NOS 1, 2, 3 or 4. In addition, the invention also comprises the nucleic acids encoding the variants of the amino acid sequences as described hereinabove.

The invention also comprises cells and expression vectors comprising nucleic acids encoding the binding compound of the invention.

Further, the invention comprises a method of producing a binding compound of the invention comprising: (a) culturing the host cell comprising a nucleic acid encoding an antibody or antibody fragment of the invention in culture medium under conditions wherein the nucleic acid sequence is expressed, thereby producing polypeptides comprising the light and heavy chain variable regions; and (b) recovering the polypeptides from the host cell or culture medium.

The invention also comprises compositions comprising a binding compound of the invention in combination with a pharmaceutically acceptable carrier or diluent.

The invention also comprises a method of inhibiting the proliferation and/or survival of an immune cell, comprising administering to a subject in need thereof a therapeutically effective amount of a binding compound of the invention. In one embodiment, the method may be used to treat cancer. In another embodiment, the method may be use to treat an autoimmune or inflammatory disease.

In some embodiments, the invention comprises a method of inhibiting the proliferation and/or survival of an immune cell, comprising administering to a subject in need thereof a therapeutically effective amount of a binding compound of the invention, and further comprising measuring B cell proliferation and/or survival ex vivo in a sample derived from the subject, wherein an inhibition of the proliferation and/or survival of the B cell indicates that the treatment should be continued.

In other embodiments, the invention comprises a method of inhibiting the proliferation and/or survival of an immune cell, comprising administering to a subject in need thereof a therapeutically effective amount of a binding compound of the invention, and further comprising measuring B cell proliferation and/or survival ex vivo in a sample derived from the subject, wherein an increase in B cell proliferation and/or survival predicts the likelihood that the treatment will be successful.

The invention also comprises an immunoconjugate comprising an anti-APRIL binding compound of the invention, linked to a therapeutic agent such as a bacterial toxin or a radiotoxin. Non-limiting examples of cytotoxic agents include taxol, cytochalasin B, mitomycin, etoposide and vincristine or other antimetabolites, alkylating agents, antibiotics and antimitotics.

The invention also comprises a method of inhibiting the proliferation and/or survival of an immune cell, comprising contacting an immune cell with a binding compound of the present invention.

In some embodiments the method comprises further administering a second therapeutic agent or treatment modality.

In some embodiments, anti-APRIL binding compounds can be combined with a treatment that is considered to be standard of care in cancer or autoimmune or inflammatory disease. Rationale for such combinations is that concurrent increased immune inhibition by anti-APRIL will induce or facilitate initial clinical response to standard of care treatment, induce durable clinical response and long-term immune control of disease.

In another embodiment the binding compounds of the present invention are used diagnostically.

In yet another embodiment the binding compounds of the invention are used to measure B cell proliferation and/or survival ex vivo in a sample derived from the subject, wherein an inhibition of the proliferation and/or survival of the B cell indicates that the treatment with the binding compound as described here above should be continued.

In another embodiment the binding compounds according to the invention are isolated antibodies or antibody fragments which bind to human APRIL.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1A shows hAPRIL.01A and hAPRIL.03A binding to FLAG-hAPRIL captured by an anti-FLAG antibody. Aprily-5 antibody was used as a positive control. FIG. 1B demonstrates that hAPRIL.01A and hAPRIL.03A hybridoma supernatants, and not Aprily-5 block the binding of FLAG-hAPRIL to BCMA-Fc.

FIG. 2A confirms binding of purified hAPRIL.01A and hAPRIL.03A to FLAG-hAPRIL, captured by an anti-FLAG antibody. FIG. 2B shows that only hAPRIL.03A binds FLAG-hAPRIL that is captured by BCMA-Fc. FIG. 2C shows that hAPRIL.01A fully blocks FLAG-hAPRIL binding to BCMA-Fc, while hAPRIL.03A partially blocks this interaction. FIG. 2D demonstrates that hAPRIL.01A and hAPRIL.03A both fully block FLAG-hAPRIL with TACI-Fc.

FIGS. 4A-B show that hAPRIL.01A and hAPRIL.03A block APRIL-driven B-cell proliferation and isotype class-switching but do not affect BAFF-mediated processes. FIG. 4A is an in-vitro B-cell assay which demonstrates that the described monoclonal antibodies block known APRIL functions such as the survival and proliferation of B cells and production of class-switched IgA antibodies. Of significance is the demonstration that both monoclonal antibodies block APRIL activity more effectively than TACI-Fc, which was administered at equimolar concentration. FIG. 4B shows that the antibodies do not affect BAFF-driven B cells responses, while TACI-Fc blocks these processes.

FIGS. 5A-B shows the results of targeting APRIL with hAPRIL.01A and hAPRIL.03A (panel A) or TACI-Fc (panel B) in-vivo, in a T-independent B cell response. Transgenic mice were challenged with NP-Ficoll, and treated with hAPRIL.01A, hAPRIL.03A and TACI-Fc twice per week. PBS and mouse IgG1 were used as negative controls. The immunoglobulin titres (IgA, IgM and IgG) were measured by ELISA. hAPRIL.01A, hAPRIL.03A and to a lesser extent TACI-Fc are able to inhibit APRIL mediated B cell responses in the hAPRIL transgenic mice and reduce immunoglobulin levels to that of the WT.

FIGS. 6A-B show the effect of targeting APRIL with hAPRIL.01A, hAPRIL.03A and TACI-Fc on B-cell populations in the spleen (panel A) or peritoneal cavity (panel B). Transgenic mice were challenged with NP-Ficoll, and treated with hAPRIL.01A, hAPRIL.03A, TACI-Fc twice per week. PBS and mouse IgG1 were used as negative controls. After 30 days of treatment, spleens and cells from the peritoneal cavity were harvested and analyzed by flow cytometry. Treatment with hAPRIL.01A or hAPRIL.03A did not affect the (sub) population of B-cells in the spleen. In contrast, TACI-Fc strongly reduced the total B-cell population and mature and T2 subpopulations. In the peritoneal cavity, TACI-Fc affected the ratio of B1 vs. B2-cells, while hAPRIL.01A and hAPRIL.03A did not affect these subpopulations.

FIGS. 7A-7D show the variable region sequences of hAPRIL.01A and hAPRIL.03A. FIGS. 7A and 7B show the amino acid sequences of the heavy (SEQ ID NO: 5) and light (SEQ ID NO: 6) chain variable sequence of hAPRIL.01A, respectively. FIGS. 7C and 7D shows the amino acid sequences of the heavy (SEQ ID NO: 7) and light (SEQ ID NO: 8) chain variable sequence of hAPRIL.03A, respectively.

DETAILED DESCRIPTION

Figure 1:
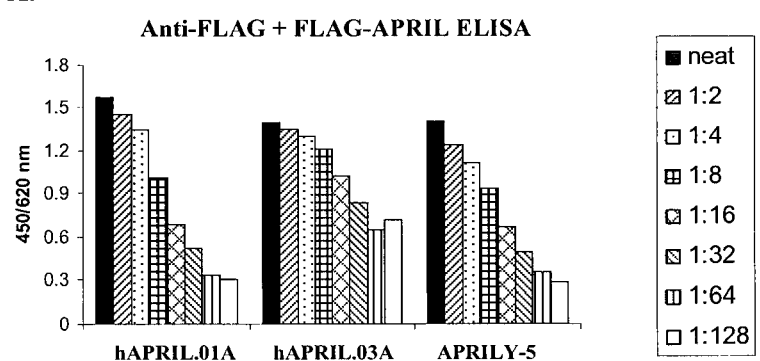
FIGS. 1A-1B show APRIL reactivity and BCMA-blocking activity of hAPRIL.01A and hAPRIL.03A hybridoma supernatants.
Figure 1:
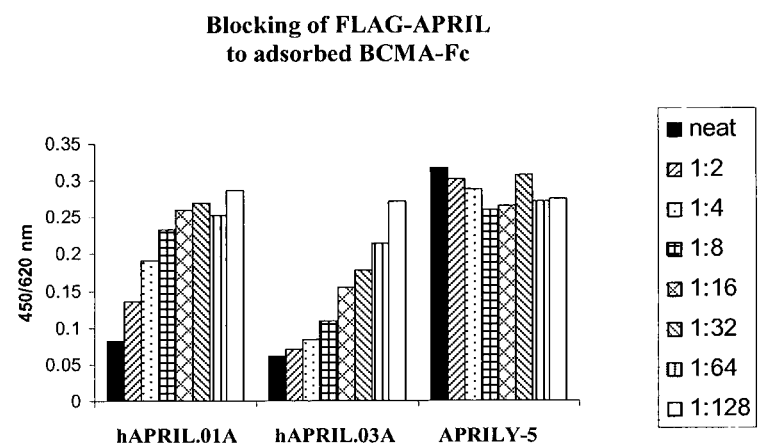

The term "antibody" refers to any form of antibody that exhibits the desired biological activity, such as inhibiting binding of a ligand to its receptor, or by inhibiting ligand-induced signaling of a receptor. Thus, "antibody" is used in the broadest sense and specifically covers, but is not limited to, monoclonal antibodies (including full length monoclonal antibodies), polyclonal antibodies, and multispecific antibodies (e.g., bispecific antibodies).

"Antibody fragment" and "antibody binding fragment" mean antigen-binding fragments and analogues of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Examples of antibody fragments include, but are not limited to, Fab, Fab', F(ab')$_2$, and Fv fragments; diabodies; linear antibodies; single-chain antibody molecules, e.g., sc-Fv, unibodies (technology from Genmab); nanobodies (technology from Domantis); domain antibodies (technology from Ablynx); and multispecific antibodies formed from antibody fragments. Engineered antibody variants are reviewed in Holliger and Hudson, 2005, *Nat. Biotechnol.* 23, 1126-1136.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the CH3 domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun, 1994, THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al., 1993, *Proc. Natl. Acad. Sci. USA* 90, 6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

As used herein antibody hAPRIL.01A is a mouse antibody wherein the heavy chain has the variable region sequence of SEQ ID NO: 5 and is joined to a IgG1 constant region and the light chain has the variable region sequence of SEQ ID NO: 6 and is joined to the κ constant region. Antibody hAPRIL.03A is a mouse antibody, wherein the heavy chain has the variable region sequence of SEQ ID NO: 7 and is joined to a IgG1 constant region and the light chain has the variable region sequence of SEQ ID NO: 8 and is joined to the κ constant region.

An antibody fragment of the invention may comprise a sufficient portion of the constant region to permit dimerization (or multimerization) of heavy chains that have reduced disulfide linkage capability, for example where at least one of the hinge cysteines normally involved in inter-heavy chain disulfide linkage is altered as described herein. In another embodiment, an antibody fragment, for example one that comprises the Fc region, retains at least one of the biological functions normally associated with the Fc region when present in an intact antibody, such as FcRn binding, antibody half life modulation, ADCC (antibody dependent cellular cytotoxicity) function, and/or complement binding (for example, where the antibody has a glycosylation profile necessary for ADCC function or complement binding).

The term "chimeric" antibody refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See, for example, U.S. Pat. No. 4,816,567 and Morrison et al., 1984, *Proc. Natl. Acad. Sci. USA* 81, 6851-6855).

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will essentially comprise the same CDR sequences of the parental rodent antibodies, although certain amino acid substitutions may be included to increase affinity, increase stability of the humanized antibody, or for other reasons. However, as CDR loop exchanges do not uniformly result in an antibody with the same binding properties as the antibody of origin, changes in framework residues (FR), residues involved in CDR loop support, might also be introduced in humanized antibodies to preserve antigen binding affinity (Kabat et al., 1991, *J. Immunol.* 147, 1709).

The term "antibody" also includes "fully human" antibodies, i.e., antibodies that comprise human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods. Also, recombinant immunoglobulins may also be made in transgenic mice. See Mendez et al., 1997, *Nature Genetics* 15, 146-156. See also Abgenix and Medarex technologies.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta, 2006, *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta, 2005, *J. Allergy Clin. Immunol.* 116, 731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in the a targeted cell.

The antibodies may also be conjugated (e.g., covalently linked) to molecules that improve stability of the antibody during storage or increase the half-life of the antibody in vivo. Examples of molecules that increase the half-life are albumin (e.g., human serum albumin) and polyethylene glycol (PEG). Albumin-linked and PEGylated derivatives of antibodies can be prepared using techniques well known in the art. See, e.g., Chapman, 2002, *Adv. Drug Deliv. Rev.* 54, 531-545; Anderson and Tomasi, 1988, *J. Immunol. Methods* 109, 37-42; Suzuki et al., 1984, *Biochim. Biophys. Acta* 788, 248-255; and Brekke and Sandlie, 2003, *Nature Rev.* 2, 52-62.

Antibodies used in the present invention will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M. See, e.g., Presta, et al., 2001, *Thromb. Haemost.* 85, 379-389; Yang, et al., 2001, *Crit. Rev. Oncol. Hematol.* 38, 17-23; Carnahan, et al., 2003, *Clin. Cancer Res.* (Suppl.) 9 3982s-3990s.

Antibody affinities may be determined using standard analysis.

The term "hypervariable region," as used herein, refers to the amino acid residues of an antibody which are responsible for antigen-binding. The hypervariable region comprises amino acid residues from a "complementarity determining region" or "CDR," defined by sequence alignment, for example residues 24-34 (L1), 50-56 (L2) and 89-97 (L3) in the light chain variable domain and 31-35 (H1), 50-65 (H2) and 95-102 (H3) in the heavy chain variable domain; see Kabat et al., 1991, Sequences of proteins of Immunological Interest, 5th Ed. Public Health Service, National Institutes of Health, Bethesda, Md. and/or those residues from a "hypervariable loop" (HVL), as defined structurally, for example, residues 26-32 (L1), 50-52 (L2) and 91-96 (L3) in the light chain variable domain and 26-32 (H1), 53-55 (H2) and 96-101 (H3) in the heavy chain variable domain; see Chothia and Leskl, 1987, *J. Mol. Biol.* 196, 901-917. "Framework" or "FR" residues are those variable domain residues other than the hypervariable region residues as herein defined.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256, 495, or may be made by recombinant DNA methods (see, for example, U.S. Pat. No. 4,816,567). The "monoclonal antibodies" may also be isolated from phage antibody libraries using the techniques described in Clackson et al., 1991, *Nature* 352, 624-628 and Marks et al., 1991, *J. Mol. Biol.* 222, 581-597, for example. The monoclonal antibodies herein specifically include "chimeric" antibodies.

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, an "immunoconjugate" refers to an anti-APRIL antibody, or a fragment thereof, conjugated to a therapeutic moiety, such as a bacterial toxin, a cytotoxic drug or a radiotoxin. Toxic moieties can be conjugated to antibodies of the invention using methods available in the art.

As used herein, a sequence "variant" refers to a sequence that differs from the disclosed sequence at one or more amino acid residues but which retains the biological activity of the resulting molecule.

"Conservatively modified variants" or "conservative amino acid substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth below as follows:

Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the term "about" refers to a value that is within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

"Specifically" binds, when referring to a ligand/receptor, antibody/antigen, or other binding pair, indicates a binding reaction which is determinative of the presence of the protein, e.g., APRIL, in a heterogeneous population of proteins and/or other biologics. Thus, under designated conditions, a specified ligand/antigen binds to a particular receptor/antibody and does not bind in a significant amount to other proteins present in the sample.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell.

Monoclonal Antibodies

Monoclonal antibodies to human APRIL can be made according to knowledge and skill in the art of injecting test subjects with human APRIL antigen and then isolating hybridomas expressing antibodies having the desired sequence or functional characteristics.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., 1990, *Nature*, 348, 552-554. Clackson et al., 1991, *Nature*, 352, 624-628, and Marks et al., 1991, *J. Mol. Biol.* 222, 581-597 describe the isolation of murine and human antibodies, respectively, using phage libraries. Subsequent publications describe the production of high affinity (nM range) human antibodies by chain shuffling (Marks et al., 1992, *Bio/Technology*, 10, 779-783), as well as combinatorial infection and in vivo recombination as a strategy for constructing very large phage libraries (Waterhouse et al., 1993, *Nuc. Acids. Res.* 21, 2265-2266). Thus, these techniques are viable alternatives to traditional monoclonal antibody hybridoma techniques for isolation of monoclonal antibodies.

Chimeric Antibodies

The antibody DNA also may be modified, for example, by substituting the coding sequence for human heavy- and light-chain constant domains in place of the homologous murine sequences (U.S. Pat. No. 4,816,567; Morrison, et al., 1984, *Proc. Natl Acad. Sci. USA*, 81, 6851), or by covalently joining to the immunoglobulin coding sequence all or part of the coding sequence for non-immunoglobulin material (e.g., protein domains). Typically such non-immunoglobulin material is substituted for the constant domains of an antibody, or is substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

A humanized antibody has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, *Nature* 321, 522-525; Riechmann et al., 1988, *Nature,* 332, 323-327; Verhoeyen et al., 1988, *Science* 239, 1534-1536), by substituting rodent CDRs or CDR sequences for the corresponding sequences of a human antibody. Accordingly, such "humanized" antibodies are antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., 1987, *J. Immunol.* 151, 2296; Chothia et al., 1987, *J. Mol. Biol.* 196, 901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA* 89, 4285; Presta et al., 1993, *J. Immnol.* 151, 2623).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Humanization of antibodies is a straightforward protein engineering task. Nearly all murine antibodies can be humanized by CDR grafting, resulting in the retention of antigen binding. See, Lo, Benny, K. C., editor, in *Antibody Engineering: Methods and Protocols*, volume 248, Humana Press, New Jersey, 2004.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA* 90, 2551; Jakobovits et al., 1993, *Nature* 362, 255-258; Bruggermann et al., 1993, *Year in Immunology* 7, 33; and Duchosal et al., 1992, *Nature* 355, 258. Human antibodies can also be derived from phage-display libraries (Hoogenboom et al., 1991, *J. Mol. Biol.* 227, 381; Marks et al., *J. Mol. Biol.* 1991, 222, 581-597; Vaughan et al., 1996, *Nature Biotech* 14, 309).

Amino acid sequence variants of humanized anti-APRIL antibodies are prepared by introducing appropriate nucleotide changes into the humanized anti-APRIL antibodies' DNAs, or by peptide synthesis. Such variants include, for example, deletions from, and/or insertions into, and/or substitutions of, residues within the amino acid sequences shown for the humanized anti-APRIL antibodies. Any combination of deletion, insertion, and substitution is made to arrive at the final construct, provided that the final construct possesses the desired characteristics. The amino acid changes also may alter post-translational processes of the humanized anti-APRIL antibodies, such as changing the number or position of glycosylation sites.

A useful method for identification of certain residues or regions of the humanized anti-APRIL antibodies polypeptides that are preferred locations for mutagenesis is called "alanine scanning mutagenesis," as described by Cunningham and Wells, 1989, *Science* 244, 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with APRIL antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-APRIL antibodies' variants are screened for the desired activity.

Ordinarily, amino acid sequence variants of the humanized anti-APRIL antibodies will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Antibodies having the characteristics identified herein as being desirable in humanized anti-APRIL antibodies can be screened for inhibitory biologic activity in vitro or suitable binding affinity. To screen for antibodies that bind to the BCMA or TACI epitopes on human APRIL bound by an antibody of interest (e.g., those that block binding of APRIL), a routine cross-blocking assay such as that described in Antibodies, A Laboratory Manual, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al., 1995, *J. Biol. Chem.* 270, 1388-1394, can be performed to determine whether the antibody binds an epitope of interest. "Alanine scanning mutagenesis," as described by Cunningham and Wells, 1989, *Science* 244, 1081-1085, or some other form of point mutagenesis of amino acid residues in human APRIL may also be used to determine the functional epitope for anti-APRIL antibodies of the present invention.

Additional antibodies binding to the same epitope as an antibody of the present invention may be obtained, for example, by screening of antibodies raised against APRIL for binding to the epitope, or by immunization of an animal with a peptide comprising a fragment of human APRIL comprising the epitope sequences (e.g., BCMA or TACI). Antibodies that bind to the same functional epitope might be expected to exhibit similar biological activities, such as blocking receptor binding, and such activities can be confirmed by functional assays of the antibodies.

Antibody affinities may be determined using standard analysis. Preferred binding compounds such as e.g. humanized antibodies are those that bind human APRIL with a $K_d$ value of no more than about $1 \times 10^{-7}$; preferably no more than about $1 \times 10^{-8}$; more preferably no more than about $1 \times 10^{-9}$; and most preferably no more than about $1 \times 10^{-10}$ or even $1 \times 10^{-11}$ M.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

The antibodies and antibody fragments of the invention may also be conjugated with cytotoxic payloads such as cytotoxic agents or radionucleotides such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$. Such antibody conjugates may be used in immunotherapy to selectively target and kill cells expressing a target (the antigen for that antibody) on their surface. Exemplary cytotoxic agents include ricin, vinca alkaloid, methotrexate, Psuedomonas exotoxin, saporin, diphtheria toxin, cisplatin, doxorubicin, abrin toxin, gelonin and pokeweed antiviral protein.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules or protein molecules of the invention to the various moieties may be employed, including those methods described by Hunter et al., 1962, Nature 144, 945; David et al., 1974, Biochemistry 13, 1014; Pain et al., 1981, J. Immunol. Meth. 40, 219; and Nygren, J., 1982, Histochem. and Cytochem. 30, 407. Methods for conjugating antibodies and proteins are conventional and well known in the art.

Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., 1992, *Bio/Technology* 10, 163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human .gamma.1, .gamma.2, or .gamma.4 heavy chains (Lindmark et al., 1983, *J. Immunol. Meth.* 62, 1-13). Protein G is recommended for all mouse isotypes and for human .gamma.3 (Guss et al., 1986, *EMBO J* 5, 1567-1575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the glycoprotein may be purified using adsorption onto a lectin substrate (e.g. a lectin affinity column) to remove fucose-containing glycoprotein from the preparation and thereby enrich for fucose-free glycoprotein.

Pharmaceutical Formulations

The invention comprises pharmaceutical formulations of an APRIL binding compound. To prepare pharmaceutical or sterile compositions, the antibody or fragment thereof is admixed with a pharmaceutically acceptable carrier or excipient, see, e.g., *Remington's Pharmaceutical Sciences* and *U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al., 2001, *Goodman and Gilman's The Pharmacological Basis of Therapeutics*, McGraw-Hill, New York, N.Y.; Gennaro, 2000, *Remington: The Science and Practice of Pharmacy*, Lippincott, Williams, and Wilkins, New York, N.Y.; Avis, et al. (eds.), 1993, *Pharmaceutical Dosage Forms: Parenteral Medications*, Marcel Dekker, NY; Lieberman, et al. (eds.), 1990, *Pharmaceutical Dosage Forms: Tablets*, Marcel Dekker, NY; Lieberman, et al. (eds.), 1990, *Pharmaceutical Dosage Forms: Disperse Systems*, Marcel Dekker, NY; Weiner and Kotkoskie, 2000, *Excipient Toxicity and Safety*, Marcel Dekker, Inc., New York, N.Y.).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration and oral administration. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternatively, one may administer the antibody in a local rather than systemic manner, for example, via injection of the antibody directly into the site of action, often in a depot or sustained release formulation. Furthermore, one may administer the antibody in a targeted drug delivery system.

Guidance in selecting appropriate doses of antibodies, cytokines, and small molecules are available (see, e.g., Wawrzynczak, 1996, *Antibody Therapy*, Bios Scientific Pub. Ltd, Oxfordshire, UK; Kresina (ed.), 1991, *Monoclonal Antibodies, Cytokines and Arthritis*, Marcel Dekker, New York, N.Y.; Bach (ed.), 1993, *Monoclonal Antibodies and Peptide Therapy in Autoimmune Diseases*, Marcel Dekker, New York, N.Y.; Baert, et al., 2003, *New Engl. J. Med.* 348, 601-608; Milgrom, et al., 1999, *New Engl. J. Med.* 341, 1966-1973; Slamon, et al., 2001, *New Engl. J. Med.* 344, 783-792; Beniaminovitz, et al., 2000, *New Engl. J. Med.* 342, 613-619; Ghosh, et al., 2003, *New Engl. J. Med.* 348, 24-32; Lipsky, et al., 2000, *New Engl. J. Med.* 343, 1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al., 2003, *New Engl. J. Med.* 349, 427-434; Herold, et al., 2002, *New Engl. J. Med.* 346, 1692-1698; Liu, et al., 1999, *J. Neurol. Neurosurg. Psych.* 67, 451-456; Portielji, et al., 2003, *Cancer Immunol. Immunother.* 52, 133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with disease and/or a reduction in the severity of such symptoms that will or are expected to develop with said disease. The terms further include ameliorating existing symptoms, preventing additional symptoms, and ameliorating or preventing the underlying causes of such symptoms. Thus, the terms denote that a beneficial result has been conferred on a vertebrate subject with a disease.

As used herein, the term "therapeutically effective amount" or "effective amount" refers to an amount of an anti-APRIL antibody or fragment thereof, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent are well known in the art, see, e.g., Hardman, et al. (eds.), 2001, *Goodman and Gilman's The Pharmacological Basis of Therapeutics*, 10th ed., McGraw-Hill, New York, N.Y.; Poole and Peterson (eds.), 2001, *Pharmacotherapeutics for Advanced Practice: A Practical Approach*, Lippincott, Williams & Wilkins, Phila., Pa.; Chabner and Longo (eds.), 2001, *Cancer Chemotherapy and Biotherapy*, Lippincott, Williams & Wilkins, Phila., Pa.

The pharmaceutical composition of the invention may also contain other agent, including but not limited to a cytotoxic, chemotherapeutic, cytostatic, anti-angiogenic or antimetabolite agent, a tumor targeted agent, an immune stimulating or immune modulating agent or an antibody conjugated to a cytotoxic, cytostatic, or otherwise toxic agent. The pharmaceutical composition can also be employed with other therapeutic modalities such as surgery, chemotherapy and radiation.

Therapeutic Uses for the Antibody and Antibody Fragments of the Invention

The antibodies and antigen binding fragments of the invention, which specifically bind to human APRIL, can be used to treat several diseases in which the activity of APRIL is central to pathology. Broadly speaking this includes cancer, autoimmunity, inflammatory diseases and potentially multiple sclerosis, a CNS disease.

Cancer

The antibody or antigen binding fragments of the invention which specifically bind APRIL can be used to treat cancer. Preferred cancers whose growth and survival may be inhibited by the invention include any cancers known to express APRIL and depend on this for proliferative signals. Non-limiting examples of such cancers include several B cell malignancies, such as Chronic Lymphocytic Leukaemia (CLL), Multiple Myeloma, Hodgkin's lymphoma and Non-Hodgkin's lymphoma including Burkitt's lumphoma and diffuse large B cell lymphoma, and also potentially several solid tumors such as glioblastomas, where APRIL expression has been reported.

The binding compounds of the invention may be used alone or in combination with other anti-cancer agents, such as chemotherapeutic reagents or other biological agents. Additionally the invention includes refractory or recurrent malignancies or treatment of metastases derived from any of these malignancies.

Autoimmune Disease

The binding compounds of the invention may be used to treat several autoimmune diseases, where the expression of APRIL has been shown to play a role in pathology. Examples of such diseases are Rheumatoid Arthritis (RA), Systemic Lupus Erythematosus (SLE) and Sjogren's syndrome. In addition, higher than normal titres of APRIL were found in the serum of multiple sclerosis patients and also increased levels were found in their astrocytes. Thus, APRIL is a contributing factor to disease pathology and therapeutic blockage of APRIL in MS may be beneficial.

Non-Therapeutic Uses for the Antibody and Antibody Fragments of the Invention

The non-therapeutic uses for these antibodies include flow cytometry, western blotting, enzyme linked immunosorbant assay (ELISA), immunohistochemistry.

The antibodies of this invention may also be used as an affinity purification reagent via immobilization to a sepharose column.

The antibody may also be useful in diagnostic assays, e.g., for detecting expression of APRIL in specific cells, tissues, or serum. For diagnostic applications, the antibody typically will be labeled (either directly or indirectly) with a detectable moiety. Numerous labels are available which can be generally grouped into the following categories: biotin, fluorochromes, radionucleotides, enzymes, iodine, and biosynthetic labels.

The antibodies of the present invention may be employed in any known assay method, such as competitive binding assays, direct and indirect sandwich assays, and immunoprecipitation assays. Zola, *Monoclonal Antibodies. A Manual of Techniques*, pp. 147-158 (CRC Press, Inc. 1987).

The antibody may also be used for in vivo diagnostic assays. Generally, the antibody is labeled with a radionuclide so that the antigen or cells expressing it can be localized using immunoscintiography or positron emission tomography.

The invention will now be further described by way of the following non-limiting examples.

EXAMPLES

Example 1

Immunization and Selection of Anti-APRIL Antibodies

Immunization of Mice with APRIL cDNA

To generate antibodies against the human APRIL protein, a cDNA encoding the full length open reading frame of APRIL was subcloned into the pCI-neo vector (Promega, Madison, Wis.). Expression of the obtained vector was checked by transient transfection of pCI-neo-hAPRIL in 293 cells (American Type Culture Collection, Manassas, Va.) and immunoblotting with mouse anti-hAPRIL IgG1 Aprily-5 (1:5,000) (Alexis, San Diego, Calif.), followed by goat anti-mouse IgG1-HRP (1:2,000) (Southern Biotechnology, Birmingham, Ala.).

Mice were immunized by gene gun immunization using a Helios Gene gun (BioRad, Hercules, Calif.) and DNA coated gold bullets (BioRad) following manufacturer's instructions. Briefly, 1 µm gold particles were coated with pCI-neo-hAPRIL cDNA and commercial expression vectors for mouse Flt3L and mouse GM-CSF in a 2:1:1 ratio (both from Aldevron, Fargo, N.Dak.). A total of 1 µg of plasmid DNA was used to coat 500 µg of gold bullets.

Specifically, 7-8 weeks old female BALB/C mice were immunized in the ears with a gene gun, receiving 4 or 5 cycles of a shot in both ears. Approximately, a 1:3,200 anti-hAPRIL titer was detected by ELISA in mouse serum after three DNA immunizations In the ELISA, all incubation steps were followed by a wash step with PBST (PBS with 0.1% Tween 20) 3 times. Maxisorp 96-well immunoplates (Nunc, Rochester, N.Y.) were coated with rabbit anti-FLAG polyclonal antibody (50 ng/well in PBS) (Sigma, St. Louis, Mo.) overnight at 4° C. and blocked with 10% Goat serum/PBST for 1 hour at RT. Plates were incubated with supernatant (1:4 in PBS) from 293T cells transiently transfected with CMV promoter driven secreted form of FLAG-hAPRIL (pCR3-hAPRIL) for 1 h at RT, followed by incubations with mouse sera dilutions and 1:2,000 HRP-conjugated goat anti-mouse IgG (Southern Biotechnology) for 1 hour each at RT. After the final PBST wash, anti-hAPRIL immunoreactivity was visualized with 100 µl OptiEIA TMB substrate (BD Biosciences, Franklin Lake, N.J.). Reactions were stopped with 100 µl 0.5 M $H_2SO_4$ and absorbances were read at 460 and 620 nm. Mice that demonstrated reactivity against hAPRIL were immunized for a final, fourth time and sacrificed four days later. Erythrocyte-depleted spleen cell populations were prepared as described previously (Steenbakkers et al., 1992, *J. Immunol. Meth.* 152: 69-77; Steenbakkers et al., 1994, *Mol. Biol. Rep.* 19: 125-134) and frozen at −140° C.

Selection of Anti-APRIL Antibody Producing B Cells

To select B cell clones producing anti-APRIL antibodies, $1.5 \times 10^7$ erythrocyte-depleted splenocytes were subjected to two rounds of negative panning on $2.3 \times 10^7$ Dynabeads® M-450 tosyl-activated beads (Invitrogen, Carlsbad, Calif.) coated with anti-FLAG M2 antibody (Sigma). 50 µg anti-FLAG M2 antibody was coated per $1 \times 10^8$ beads in 500 µl according to manufacturer's instructions. Beads and splenocyte suspension were incubated for 30 minutes on ice and resuspended in cold DMEM F12/P/S/10% BCS. Unbound splenocytes were separated from the beads using the Dynal MPC (Magnetic Particle Concentrator) (Invitrogen). For the positive panning, splenocytes were incubated with $2.3 \times 10^7$ beads coated with anti-FLAG M2 bound to FLAG-hAPRIL for 30 minutes on ice. Beads and unbound splenocytes were separated as described above with a total of 12 washes.

Antigen-specific B-cells were cultured as described by Steenbakkers et al., 1994, Mol. Biol. Rep. 19: 125-134. Briefly, selected B-cells were mixed with 7.5% (v/v) T-cell supernatant and 50,000 irradiated (2,500 RAD) EL-4 B5 nursing cells in a final volume of 200 μl DMEM F12/P/S/10% BCS in a 96-well flat-bottom tissue culture plates. On day eight, supernatants were screened for hAPRIL reactivity by ELISA as described above. 21 APRIL-reactive supernatants were identified and tested for their ability to inhibit the interaction of APRIL with BCMA-Fc. In the ELISA, all incubation steps were followed by a wash step with PBST (PBS with 0.1% Tween 20) 3 times. A Maxisorp 96-well immunoplate was coated with BCMA-Fc (50 ng/well in PBS) (R&D Systems, Minneapolis, Minn.) overnight at 4° C. and blocked with 10% Goat serum/PBST for 1 hour at RT. FLAG-hAPRIL containing supernatants were pre-incubated with antibody-containing B-cell supernatants for 1 hour at RT and then added to the BCMA-Fc coated plate for 1 hour at RT. Bound FLAG-hAPRIL was detected by incubation with 1 μg/ml anti-FLAG BioM2-biotin antibody (Sigma) and 1:2,000 Streptavidin-HRP (Southern Biotechnology) for 1 hour each at RT. After the final PBST wash, APRIL-bound BCMA-Fc was visualized with 100 μl OptiEIA TMB substrate (BD Biosciences). Reactions were stopped with 100 μl 0.5 M $H_2SO_4$, and absorbances were read at 460 and 620 nm.

Subsequently, 8 B-cell clones were immortalized by minielectrofusion following published procedures (Steenbakkers et al., 1992, *J. Immunol. Meth.* 152, 69-77; Steenbakkers et al., 1994, *Mol. Biol. Rep.* 19, 125-34). Specifically, B-cells were mixed with $10^6$ NS-1 myeloma cells, and serum was removed by washing with DMEM F12 media. Cells were treated with pronase solution for three minutes and washed with fusion medium. Electrofusions were performed in a 50 μl fusion chamber by an alternating electric field of 30 s, 2 MHz, 400 V/cm followed by a square, high field pulse of 10 μs, 3 kV/cm and again by an alternating electric field of 30 s, 2 MHz, 400 V/cm. Contents of the chamber were transferred to hybridoma selective medium and plated in a 96-well plate under limiting dilution conditions. On day 14 following the fusions, hybridoma supernatants were screened for APRIL reactivity and BCMA-blocking activity, as described above. Two distinct anti-hAPRIL hybridomas, named hAPRIL.01A and hAPRIL.03A were isolated and subcloned by limited dilution to safeguard their integrity. hAPRIL reactivity and BCMA-blocking activity of hAPRIL.01A and hAPRIL.03A antibodies were confirmed with hybridoma supernatants (see FIG. 1).

Example 2

Purification and Characterization of Anti-APRIL Antibodies

Stabilization of Anti-APRIL Producing Hybridomas and Purification of Anti-APRIL Antibodies Clonal cell populations were obtained for each hybridoma by multiple rounds of limiting dilutions (six for hAPRIL.01A and four for hAPRIL.03A). Stable hybridomas were cultured in serum-free media using CELLine® bioreactors (Integra-Biosciences, Chur, Switzerland) according to manufacturer's instructions. Following 7-10 days in culture, supernatants were harvested and filtered through a 0.22 .mu.M nitrocellulose membrane. Supernatants were diluted 1:1 in high salt binding buffer (1 M Glycine/2M NaCl, pH 9.0), and antibodies were purified with Protein G HiTrap 5 ml columns (GE Healthcare, Piscataway, N.J.). After PBS wash of the column, antibodies were eluted with 0.1 M Glycine pH 2.7 and neutralized with 3 M Tris. Buffer was exchanged for PBS using PD-10 gel-filtration columns (GE Healthcare). Antibodies were concentrated with Amicon Ultra-15 centrifugal filter units (Millipore, Billerica, Mass.) and quantified using spectrophotometry.

Using a mouse monoclonal antibody isotyping test kit (Serotec, Raleigh, N.C.), the (sub)-isotype of both hAPRIL.01A and hAPRIL.03A antibodies was determined to be IgG1, Kappa.

Binding Analysis

Protein-based ELISA experiments using purified hAPRIL.01A and hAPRIL.03A antibodies were performed to determine apparent binding affinities (reported as $EC_{50}$ values). Binding was compared to mouse anti-hAPRIL IgG1 Aprily-5 (Alexis). Maxisorp 96-well immunoplates (Nunc) were coated with either rabbit anti-FLAG polyclonal antibody (Sigma) or BCMA-Fc (R&D Systems) at 50 ng/well in PBS overnight at 4° C. and blocked with 10% Goat serum/PBST for 1 hour at RT. Plates were washed with PBST 3 times and incubated with supernatant (1:4 in PBS) containing FLAG-hAPRIL for 1 hour at RT. Plates were again washed with PBST 3 times and incubated with hAPRIL.01A, hAPRIL.03A, and Aprily-5 antibodies (10 μg/ml high test with 10-fold dilutions in triplicates) for 1 h at RT. After three washes with PBST, bound antibodies were detected with goat anti-mouse IgG-HRP (1:2,000) (Southern Biotechnology) for 1 hour at RT. Plate was washed three times with PBST, and APRIL-reactivity was visualized with OptiEIA TMB substrate (Becton Dickinson). The concentration for half-maximal binding is reported as a measure of relative binding affinity. When FLAG-hAPRIL was captured by the anti-FLAG antibody (FIG. 2A), $EC_{50}$ values for hAPRIL.01A, hAPRIL.03A and Aprily-5 were calculated as 2.2, 1.4, and 1.7 nM, respectively. When FLAG-hAPRIL was captured by BCMA-Fc (FIG. 2B), hAPRIL.01A antibody binding was not observed, suggesting that the APRIL-BCMA interaction blocked the hAPRIL.01A epitope. In contrast, binding of hAPRIL.03A to the APRIL-BCMA complex was observed. Antibody detection of the receptor-ligand complex may prove useful in diagnostic assays and for research purposes to follow the clearance of soluble APRIL.

Kinetic Analysis by Bio-Light Interferometry (ForteBio)

To further characterize the binding characteristics of the antibodies, each was profiled using bio-light interferometry on the Octet system (ForteBio, Menlo Park, Calif.) to elucidate binding kinetics and calculate equilibrium binding constants. This assay was performed by coupling purified hAPRIL.01A and hAPRIL.03A antibodies to amine-reactive biosensors (Fortebio) using standard amine chemistry. Recombinant human APRIL (R&D Systems) binding to and dissociation from the biosensors was then observed at two concentrations, 1 and 2 μg/ml. Specifically, amine-reactive biosensors were pre-wetted by immersing them in wells containing 0.1 M MES pH=5 for 2 minutes. The biosensors were then activated using a 0.1 M NHS/0.4 M EDC mixture for 5 minutes. hAPRIL.01A and hAPRIL.03A antibodies were coupled by immersing the biosensors in a solution of 5 μg/mL of the antibody for 18 minutes. The biosensor surface was quenched using a solution of 1M ethanolamine pH 8.5 for 7 minutes. Biosensors were equilibrated in PBS for 5 minutes. Association of recombinant APRIL was observed by placing the biosensors in wells containing either 1 or 2 µg/ml APRIL and monitoring interferometry for 20 minutes. Dissociation was measured after transfer of the biosensors into PBS and monitoring of the interferometry signal for 20 minutes. The observed on and off rates ($k_{obs}$ and $k_d$) were fit using a 1:1 binding global fit model, and the equilibrium binding constant $K_D$ was calculated (see Table 1).

TABLE 1

Binding characteristics of humanized anti-hAPRIL antibodies of the invention

| mAb | $k_{obs}$ $M^{-1}s^{-1}$ | $k_{dissoc}$ $s^{-1}$ | $K_D$ M |
|---|---|---|---|
| hAPRIL.01A | 4.89E+04 | 3.69E−05 | 7.53E−10 |
| hAPRIL.03A | 7.54E+04 | 4.21E−05 | 5.58E−10 |

Receptor Blockade

Figure 2:
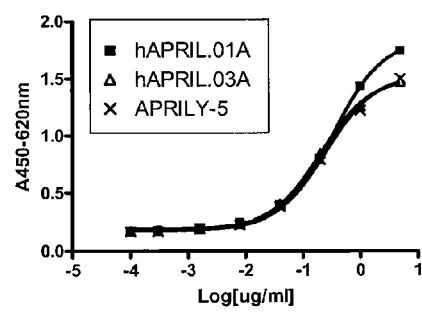
FIGS. 2A-D show distinct binding and receptor-blocking characteristics of purified hAPRIL.01A and hAPRIL.03A antibodies.
Figure 2:
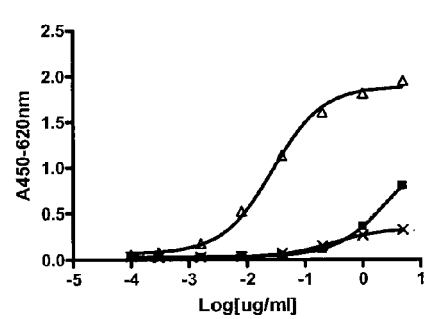
Figure 2:
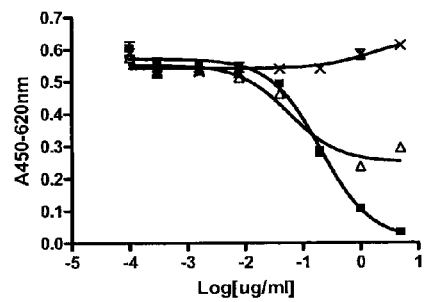
Figure 2:
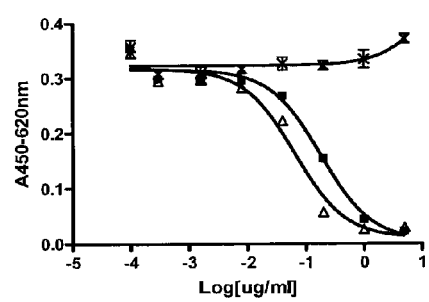

Blocking abilities of hAPRIL.01A and hAPRIL.03A were confirmed using purified antibodies. Maxisorp 96-well plates were coated with either BCMA-Fc (R&D Systems) or TACI-Fc (R&D Systems) at 50 ng/well overnight at 4° C. and blocked with 10% Goat serum/PBST for 1 hour at RT. FLAG-hAPRIL containing supernatants were pre-incubated with hAPRIL.01A, hAPRIL.03A, and Aprily-5 antibodies (10 µg/ml high test with 10-fold dilutions in triplicates) for 1 h at RT. Plates were washed with PBST 3 times, and bound FLAG-hAPRIL was detected by incubation with 1 µg/ml anti-FLAG BioM2-biotin antibody (Sigma) and 1:2,000 Streptavidin-HRP (Southern Biotechnology) for 1 hour each at RT. After the final PBST wash, APRIL-bound BCMA-Fc was visualized with OptiEIA TMB substrate (BD Biosciences). As shown in FIGS. 2C and 2D, hAPRIL.01A fully blocks FLAG-hAPRIL binding to BCMA-Fc and TACI-Fc, whereas hAPRIL.03A fully blocks FLAG-hAPRIL binding to TACI-Fc, while only partially blocking the hAPRIL-BCMA-Fc interaction. Aprily-5 does not block FLAG-hAPRIL binding to either BCMA-Fc or TACI-Fc. The concentration of half-maximum inhibition ($IC_{50}$) was determined for hAPRIL.01A as 1.2 and 0.4 nM for BCMA-Fc and TACI-Fc, respectively. The $IC_{50}$ for hAPRIL.03A to TACI-Fc was determined as 1.3 nM.

Commercial Antibodies

Commercially available anti-APRIL antibodies were obtained as described in Table 2.

TABLE 2

Commercially available anti-human APRIL monoclonal antibodies

| Antibody | Company | Cat no. |
|---|---|---|
| Aprily-1 | Alexis | ALX-804-148-C100 |
| Aprily-2 | Alexis | ALX-804-844-C100 |
| Aprily-5 | Alexis | ALX-804-801-C100 |
| Aprily-8 | Alexis | ALX-804-149-C100 |
| Sacha-1 | Alexis | ALX-804-141-C100 |
| Sacha-2 | Alexis | ALX-804-804-C100 |
| anti-CD256, clone T3-6 | BioLegend | 318502 |
| mouse anti-human APRIL | LifeSpan Biosciences | LS-C18658 |
| mouse anti-human APRIL | LifeSpan Biosciences | LS-C18659 |
| mouse anti-human APRIL | LifeSpan Biosciences | LS-C18687 |
| TNFSF13 monoclonal antibody (M01), clone H4-E8 | Tebu-bio | H00008741-M01 |
| TNFSF13 monoclonal antibody (M02), clone G3 | (ABNOVA) | H00008741-M02 |
| Human APRIL/TNFSF13 MAb (Clone 101115) | R and D | MAB884 |

Figure 3:
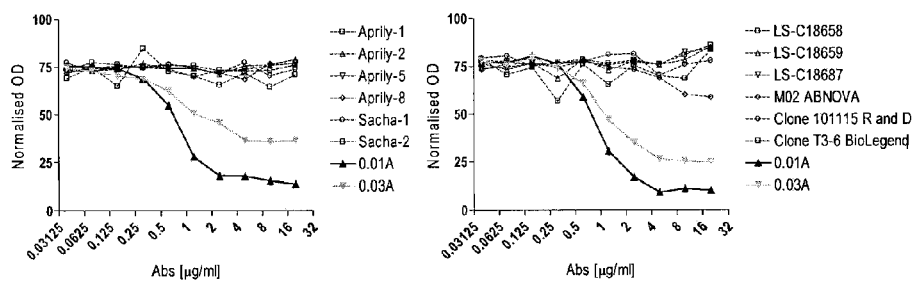
FIGS. 3A-B show the receptor-blocking ELISAs for hAPRIL.01A, hAPRIL.03A, and 12 known commercially available monoclonal anti-APRIL antibodies. This illustrates that hAPRIL.01A and hAPRIL.03A are unique in their ability to block APRIL binding to BCMA (FIG. 3A) and TACI (FIG. 3B).
Figure 3:
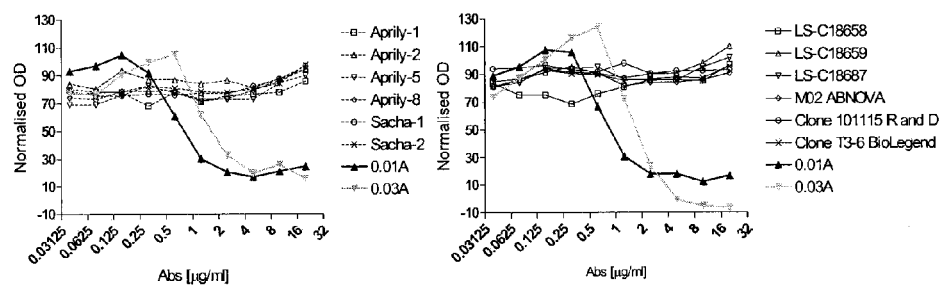

To study whether the blocking characteristics of hAPRIL.01A and hAPRIL.03A are unique, all known commercially available anti-APRIL antibodies were tested for their ability to block the interaction of FLAG-hAPRIL to BCMA-Fc and TACI-Fc (FIGS. 3A and 3B). Blockade of receptor binding was studied using an ELISA. An ELISA plate was coated with 50 with 100 µl of BCMA-Fc at 1 µg/ml or with 100 µl of TACI-Fc at a concentration of 2 µg/ml in coating buffer and incubated overnight at 4° C. The plate was then washed with PBS/0.2% Tween and then incubated with for 1 hour at 37° C. with 100 µl PBS/5% BSA per well. The plate was then washed four times with PBS/0.2% Tween. In a separate plate APRIL monoclonal antibodies were pre-mixed with APRIL supernatant and incubated for 30 minutes on ice. Conditioned medium containing soluble APRIL was diluted 1 in 4 and mixed with an equal volume of PBS containing the antibodies titrated in doubling dilutions starting with 5 µg/ml. 100 µl of the pre-incubated mix was transferred to the ELISA plate and incubated for 2 hours at 37° C. The plate was then washed four times with PBS/0.2% Tween. Anti-Flag-HRP antibody was then diluted in PBS at a concentration of 1:1000 and then 100 µl of this added to each well and incubated for 1 hour at 37° C. The plate was then washed four times with PBS/0.2% Tween and then 100 µl of ABTS added to each well (the ABTS was diluted to the ratio 10 ml of reagent plus 5 µl of $H_2O_2$ made immediately before addition). The colour was allowed to develop and then the OD at 405 nm read on an ELISA plate reader. Human IgG1 was used as a control protein to coat the plate as this is the same isotype as the Fc-fusion proteins and controlled for APRIL sticking to the plate non-specifically. As is apparent from FIG. 3, none of the commercially available antibodies was able to block the binding of FLAG-APRIL to either TACI-Fc or BCMA-Fc, whereas hAPRIL.01A and hAPRIL.03A do inhibit (partially) the binding to TACI-Fc and BCMA-Fc.

Species Cross-Reactivity

Binding of hAPRIL.01A and hAPRIL.03A to mouse APRIL was also examined by BIAcore, but no binding of either antibody was observed. The antibodies appear only to bind human APRIL.

Example 3

Functional Profiling of Murine Anti-Human APRIL Antibodies

Mouse B Cell Response to APRIL

In order to show that the antibodies of this invention can functionally block APRIL in-vitro a mouse B cell assays was used to examine two APRIL driven responses in B cells—proliferation and IgA production.

All cell lines were maintained at 37° C. with 5% $CO_2$. Mouse splenocytes and purified B cells were grown in RPMI-1640 (Gibco) supplemented with 8% FCS, 2 mM Glutamine and Beta-mercaptoethanol at 50 µM, and supplemented with penicillin and streptomycin at a concentration of 10 µg/ml.

Splenic mouse B cells were isolated from wild-type mice using magnetic activated cell separation (MACS) columns with CD45R/B220 MACS beads (Miltenyi Biotec, Utrecht, The Netherlands). The cells were cultured in 96-well round-bottomed microtiter plates at a density of $2\times10^5$/well in a final volume of 200 µl. For all assays conditioned medium containing the various forms of soluble APRIL were normalised for expression levels prior to use. To measure proliferation, cells were treated with anti-IgM (Jackson ImmunoResearch) and soluble APRIL in conditioned medium or as purified protein at a final concentration of 1 µg/ml. Cross-linking anti-Flag monoclonal antibody was added to the well at a final concentration of 1 µg/ml. The cells were incubated at 37° C. and after 48 hours pulsed with 0.3 µCi (0.011 MBq) of tritiated thymidine ([6-$^3$H] Thymidine, GE Healthcare, The Netherlands) for 18 hours, before harvesting. To measure IgA production, mouse B cells were cultured and treated with APRIL, as above. Following incubation for 6 days, supernatant was collected and assayed for IgA content by ELISA. Briefly, ELISA plates were coated with 2 µg/ml anti-mouse-Ig (Southern Biotech), blocked with PBS/1% BSA and incubated with the collected supernatant. Bound IgA was then detected with HRP labelled anti-mouse-IgA (Southern Biotech, Uithoorn, the Netherlands). As a control, cells were treated with 10 µg/ml LPS (Invivogen) plus 1 ng/ml of human TGFβ (Sigma-Aldrich). As shown in FIG. 4A, hAPRIL.01A and to a lesser extent hAPRIL.03A are able to inhibit APRIL induced class-switch recombination as was determined by the reduced IgA secretion from mouse splenic B-cells. TACI-Fc as a control inhibited the IgA secretion, while mouse IgG1 and human Ig did not affect the APRIL-induced IgA secretion from splenic B-cells. In addition, hAPRIL.01A and hAPRIL.03A were demonstrated to inhibit APRIL-induced mouse splenic B-cell proliferation. To establish the specificity of the antibodies, the effect of hAPRIL.01A and hAPRIL.03A on BAFF-induced IgA secretion and proliferation was studied. As shown in FIG. 4B, neither hAPRIL.01A nor hAPRIL.03A inhibited BAFF induced IgA secretion and proliferation, while TACI-Fc as a control inhibited both processes.

In-Vivo Experiment to Block APRIL Function

To demonstrate an in-vivo blocking effect of the antibodies on APRIL function, we examined the ability of the antibodies to block the NP-Ficoll induced humoral response in mice. The mice used were 8-10 week old APRIL transgenic (TG) mice and wildtype (WT) littermates, both on a C57BL/6 background. The APRIL transgenic mice express human APRIL under the Lck-distal promoter, which directs transgene expression to mature thymocytes and peripheral T lymphocytes (Stein et al., 2002, *J Clin Invest* 109, 1587-98). The mice were bred in the animal facility of the Academic Medical Center and the experiment was approved by the institutional ethical committee. The mice were divided into several groups and treated as follows: five APRIL WT mice were treated with PBS (200 µl) and 5 groups of five APRIL transgenic mice were treated with the following molecules: hAPRIL.01A or hAPRIL.03A or TACI-Fc or subisotype-matched control antibody msIgG1_k (200 µg/mouse in 200 µl PBS) or PBS. Treatment of the mice was started 3 days before the NP-Ficoll immunization (day 0; 100 µl i.p. with 250 µg of the immunogen)—injections were continued twice a week for 28 days. Blood was collected via tail vein at day −1, 3, 7, 14 and 28. Anti-(4-hydroxy-nitrophenacetyl) (NP)-specific antibodies (IgM, IgG and IgA) were assayed in 6 independent ELISA using diluted sera (1:100 for IgA; 1:500 for IgG and 1:2,000 for IgM) as previously described (Hardenberg et al., *Immunol Cell Biol,* 86 (6), 530-4, (2008)). Briefly 96-well ELISA plates (Greiner) were coated with NP-BSA at 5 µg/ml (Biosearch Technologies) in sodium carbonate buffer (pH 9.6) overnight at 4° C. The wells were blocked with 1% BSA for 1 hr at 37° C. and incubated with diluted sera for 2 hrs at room temperature. HRP-conjugated isotype specific antibodies (Goat anti-mouse IgG, IgA and IgM—from Southern Biotech) were used as revealing antibodies. All dilutions were made in PBS/BSA 1%/Tween 20 0.05%. One way ANOVA test was used to check statistical significance between the groups TG (PBS) vs TG (hAPRIL.01A) and TG (PBS) vs TG (hAPRIL.03A). As apparent from FIG. 5, both hAPRIL.01A and hAPRIL.03A inhibited the T-cell independent B-cell responses in vivo. TACI-Fc inhibited this response less efficient. PBS and mouse IgG1 as an isotype-matched control, did not affect the IgA, IgM and IgG anti-NP response.

To examine the long-term effect of hAPRIL.01A and hAPRIL.03A on B cell populations mice were treated as described above. On day 30, mice were sacrificed and the spleen and peritoneal exudate cavity (PEC) analysed for B cell expression by flow cytometry. Briefly, splenocytes and lymphocytes from the PEC were separated from red blood cells by one wash with erythrocyte lysis buffer and then counted. Cells were washed and resuspended in PBS/1% BSA and seeded in 96-well round-bottomed plates at a density of $5\times10^5$ per well. Next, cells were stained with the following antibodies at the recommended concentrations: B220-FITC (BD bioscience) and CD3-APC (ebioscience); IgD-FITC (BD bioscience) and IgM-PE (BD bioscience); IgD-FITC (BD bioscience), CD3-APC (ebioscience) and CD43-PE (BD bioscience). Antibodies were incubated for 40 minutes, washed three times with PBS/1% BSA and then analysed by flow cytometry using the FACSCalibur (Becton Dickenson). B220$^+$ B-cells, mature B-cells (IgD$^+$IgM$^{int}$) and T2 B-cells (IgD$^+$IgM$^+$) in spleen were quantified (see FIG. 6A). In addition, B1 (CD43$^+$IgD$^{int}$) and B2 (CD43$^-$IgD$^+$) subpopulations were quantified in PEC (see FIG. 6B). The decrease in B cells in response to TACI-Fc treatment is evident from both the spleen and the PEC, indicating that long term administration of TACI-Fc may have a detrimental effect on normal B cell populations. This is not seen with hAPRIL.01A and hAPRIL.03A antibodies, suggesting that in cases where APRIL but not BAFF is the primary cause of pathology, the antibodies of this invention may show less side-effects than TACI-Fc.

Example 4

Anti-APRIL Antibodies Sequences

Cloning of Immunoglobulin cDNAs

Degenerate primer PCR-based methods were used to determine the DNA sequences encoding the variable regions for the mouse antibodies that are expressed by hybridomas hAPRIL.01A and hAPRIL.03A. Total RNA was isolated from $5\times10^6$ hybridomas cells using TRIZOL (Invitrogen), and gene specific cDNAs for the heavy and light chains were synthesized using the iScript Select cDNA synthesis kit (Biorad) according to the manufacturer's instructions. The V$_H$ and V$_L$ genes were PCR-amplified using a Novagen-based Ig-primer set (Novagen, San Diego, Calif.) and Taq polymerase (Invitrogen). All PCR products that matched the expected amplicon size of 500 bp were cloned into pCR4 TOPO vector (Invitrogen), and the constructs were transformed in DH5α *E. coli* (Invitrogen) according to the manufacturer's instructions. Clones were screened by colony PCR using universal M13 forward and reverse primers, and two clones from each reaction were selected for DNA sequencing analysis.

Sequences were searched against databases of germline and rearranged IgV variable region sequences using the website for NCBI Ig-Blast BLASTN 2.2.16. Blast results for hAPRIL.01A and hAPRIL.03A showed one in-frame $V_H$ sequence and one in frame $V_L$ sequence for each antibody. The amino acid sequences were confirmed by mass spectrometry. The sequences are disclosed in the attached Sequence Listing, FIG. 7 and listed in Table 3.

TABLE 3

Sequence ID numbers for murine anti-human APRIL antibodies of this invention

| SEQ ID NO: | Description |
|---|---|
| 1 | hAPRIL.01A heavy chain variable region (DNA) |
| 2 | hAPRIL.01A light chain variable region (DNA) |
| 3 | hAPRIL.03A heavy chain variable region (DNA) |
| 4 | hAPRIL.03A light chain variable region (DNA) |
| 5 | hAPRIL.01A heavy chain variable region (AA) |
| 6 | hAPRIL.01A light chain variable region (AA) |
| 7 | hAPRIL.03A heavy chain variable region (AA) |
| 8 | hAPRIL.03A light chain variable region (AA) |
| 9 | hAPRIL.01A heavy chain CDR1 (AA) |
| 10 | hAPRIL.01A heavy chain CDR2 (AA) |
| 11 | hAPRIL.01A heavy chain CDR3 (AA) |
| 12 | hAPRIL.01A light chain CDR1 (AA) |
| 13 | hAPRIL.01A light chain CDR2 (AA) |
| 14 | hAPRIL.01A light chain CDR3 (AA) |
| 15 | hAPRIL.03A heavy chain CDR1 (AA) |
| 16 | hAPRIL.03A heavy chain CDR2 (AA) |
| 17 | hAPRIL.03A heavy chain CDR3 (AA) |
| 18 | hAPRIL.03A light chain CDR1 (AA) |
| 19 | hAPRIL.03A light chain CDR2 (AA) |
| 20 | hAPRIL.03A light chain CDR3 (AA) |

Example 5

Epitope Mapping Using Pepscan Method

Synthesis of Peptides and Pepscan Screening

The synthetic linear and CLIPS peptides were synthesized and screened using creditcard format mini PEPSCAN cards (455-well plate with 3 ul wells) as described by Slootstra et al. (Slootstra et al., 1996, *Mol. Diversity* 1, 87-96) and Timmerman et al. (Timmerman et al., 2007, *J. Mol. Recognit.* 20, 283-299). The binding of antibodies (hAPRIL.01A and hAPRIL.03A) to each peptide was tested in a PEPSCAN-based enzyme-linked immuno assay (ELISA). The 455-well creditcard-format polypropylene cards, containing the covalently linked peptides, were incubated with sample (for example 1 ug/ml antibody diluted in a PBS solution containing 5% horse serum (vol/vol) and 5% ovalbumin (weight/vol)) and 1% Tween 80 (4° C., overnight). After washing the peptides were incubated with an anti-antibody peroxidase (dilution 1/1000, for example rabbit anti-mouse peroxidase, Southern Biotech) (1 hour, 25° C.), and subsequently, after washing the peroxidase substrate 2,2'-azino-di-3-ethylbenzthiazoline sulfonate (ABTS) and 2, ul/ml 3% H2O2 were added. After 1 hour the color development was measured. The color development of the ELISA was quantified with a CCD-camera and an image processing system. The setup consists of a CCD-camera and a 55 mm lens (Sony CCD Video Camera XC-77RR, Nikon micro-nikkor 55 mm f/2.8 lens), a camera adaptor (Sony Camara adaptor DC-77RR) and Image Processing Software.

Synthesis Peptides

A total of 4225, primarily, CLIPS peptides were synthesized. The target sequence used, 147 amino acids, with loops according to alignment with 1XU2.pdb underlined:

RAVLTQKQKKQHSVLHLVPINA
TSKDDSDVTEVMWQPALRRGRGLQAQGYG VRI
QDAGVYLLYSQVLFQDVTFTMGQVVSRE
GQGRQETLFRCIRSMPSHPDR AYNSCYSAGVFH
LHQGDILSVIIPRARAKLNLSPHGTFLGFVKL
(SEQ ID NO:21). Loops on "top" side of protein: QKKQHSVLHL (SEQ ID NO:22), ALRRGRGL (SEQ ID NO:23), QAQGYGVRI (SEQ ID NO:24), QDAGVYLL (SEQ ID NO:25), SREGQGRQETV (SEQ ID NO:26), FHLHQGDILSV (SEQ ID NO:27) and loops on "bottom" side of protein: INATSKDDSD-VTE (SEQ ID NO:28), VLFQDVTFTMG (SEQ ID NO:29), IRSMPSHPDRAYNSC (SEQ ID NO:30), IIPRARAKL (SEQ ID NO:31), NLSPHGTFLGF (SEQ ID NO:32). The interconnecting regions are mostly sheets. Note that the "top" and "bottom" side are chosen arbitrarily.

The following CLIPS topologies were used: T2 CLIPS couples to the side-chain of two cysteines to form a single loop topology, while T3 CLIPS couples to the side-chain of three cysteines to form double loop topology, while T2T2 CLIPS first T2 couples to two cysteines (labeled C), and second T2 couples to two cysteines and finally T2T3 CLIPS T2 couples to two cysteines and T3 couples to three cysteines.

In total 20 different sets of peptides were synthesized:

191-1 (set-1): All overlapping 35-mer sequences covering the complete 147 AA target sequence were synthesized. In this set the different loops, when present in the sequence, as defined above were constrained in double loop or sheet-like topology through two T2 CLIPS.

191-2 (set-2) A total of nine sheets were identified. All 9×9 combinations were synthesized to mimic double sheet conformations. The sequence GSG was used as a linker.

191-3 (set-3) The same as set-2 as explained above but with a shorter sheet length.

191-6 (set-4) All overlapping linear 35-mer sequences covering the complete 147 AA target sequence were synthesized.

191-7 (set-5) All overlapping linear 15-mer sequences covering the complete 147 AA target sequence were synthesized.

191-8 (set-6a) Short linear sequences (of varying length) only covering the loop regions of the complete 147 AA target sequence were synthesized.

191-16 (set-6b) Different peptides were selected from the five "bottom" loops. These were recombined in a 9×9 matrix onto the T3 CLIPS to form double looped topologies with "bottom" loops of two different lengths.

191-17 (set-7) All overlapping 135 different 15-mer sequences were synthesized with a cysteine at position 1, 8 and 15. The three cysteine were coupled to a T3 CLIPS.

191-18 (set-9) Long versions of the six "top" loops and long versions of the four "bottom" loops were recombined with each other on the T3 CLIPS.

191-19 (set-10) Six+Six+Four different sized loops of the "top" loop region were all recombined with each other on the T3 CLIPS.

191-20 (set-11,17,18,19,20) 33 different sequences broadly covering the "top" or "bottom" loops were recombined with other on the T3 CLIPS. These sets of peptides are in sets 11, 17, 18, 19 and 20. Reason for this "scattering" is the card layout.

191-22 (set-12) Different sized loops of all "top" and "bottom" loops were synthesized as single loops on T2 CLIPS.

191-23 (set-13) All overlapping single looped 15-mer sequences covering the complete target protein were synthesized on T2 CLIPS.

191-24 (set-14) Six different 9-mer sequences covering the "top" loops were recombined with each in a 6×6×6 triple looped matrix on T2T3 CLIPS combination.

191-25 (set-15) The same set of overlapping peptides as set-1. All overlapping 35-mer sequences covering the complete 147AA target sequence were synthesized. In this set the different loops, when present in the sequence, as defined above were constrained into triple loop topology through T3T2 CLIPS.

191-26 (set-16) Six different 9-mer sequences covering the "bottom" loops were recombined with each in a 6×6×6 triple looped matrix on T2T3 CLIPS combination.

Data Analysis and Epitope Determination

Each antibody was tested on all 4225 peptides and their binding values were ranked. Clearly re-occurring sequences in most the top binders (~top 1%) were considered as epitope candidates. Two additional supporting analyses were done. Firstly, it was investigated if multiple identified parts can form one discontinuous epitope. This was done through the homologous structure 1XU2.pdb. Secondly, it was investigated if each of multiple identified binding parts was recognized without support of the other part. These two parameters, co-localization on the 3D structure and independent recognition, were used to support that a conformational and discontinuous epitope was identified. For hAPRIL.01A it was determined that it binds to IRSMPSHPDRA (SEQ ID NO:33), with the core region being SMPSHP (SEQ ID NO:34). The TLFR (SEQ ID NO:35) and/or QDVTFTMGQ (SEQ ID NO:36) (core region is VTFTM (SEQ ID NO:37)) motifs were shown to support the binding of hAPRIL.01A. hAPRIL.03A was shown to bind VSREGQGRQ (SEQ ID NO:38) motif, with core region being EGQ. The TFTMGQ (SEQ ID NO:39) motif was shown to support binding of hAPRIL.03A.

The invention is further described by the following numbered paragraphs:

1. A binding compound which binds to human APRIL comprising:
  a. an antibody heavy chain variable region comprising at least one CDR selected from the group consisting of SEQ ID NOs: 9, 10, 11, 15, 16 and 17, or a variant of any said sequence; and/or
  b. an antibody light chain variable region comprising at least one CDR selected from the group consisting of SEQ ID NOs: 12, 13, 14, 18, 19 and 20, or a variant of any said sequence.

2. The binding compound of paragraph 1, comprising:
  a. heavy chain CDRs SEQ ID NOs: 9, 10 and 11, or variants of any said sequences; and light chain CDRs SEQ ID NOs: 12, 13 and 14, or variants of any said sequences; or
  b. heavy chain CDRs SEQ ID NOs: 15, 16 and 17 or variants of any said sequences; and light chain CDRs SEQ ID NOs: 18, 19 and 20 or variants of any said sequences.

3. The binding compound of paragraph 1 selected from a binding compound comprising
  a. a heavy chain variable region comprising the amino acid sequence of SEQ ID NO: 5 and a light chain variable region comprising the amino acid sequence selected from the group of SEQ ID NO: 6; or
  b. a heavy chain variable region comprising the amino acid sequence of SEQ ID NO: 7 and a light chain variable region comprising the amino acid sequence selected from the group of SEQ ID NO: 8.

4. The binding compound of paragraphs 1-3, wherein any of said variant(s) may comprise up to three amino acid modifications.

5. The binding compound of any of the above paragraphs, wherein the binding compound fully blocks the binding of APRIL with human TACI and at least partially blocks the binding with human BCMA.

6. The binding compound of paragraph 5, wherein the binding compound fully blocks the binding of human April with human BCMA.

7. The binding compound of any of the above paragraphs, wherein the binding compound:
  a. binds human APRIL with a $K_D$ of about 10 nM or lower; and
  b. blocks binding of human TACI and/or human BCMA to human APRIL with an $IC_{50}$ of about 2 nM or lower.

8. A binding compound which binds to human APRIL wherein the binding compound has the same epitope specificity as the compound selected from paragraph 3.

9. A binding compound which competes for a binding epitope on human APRIL with any of the binding compounds of paragraph 3, and has one of the following characteristics:
  a. binds human APRIL with a $K_D$ of about 10 nM or lower;
  b. binds to human APRIL with about the same $K_D$ as an antibody having a heavy chain comprising the amino acid sequence of SEQ ID NO: 5 and a light chain comprising the amino acid sequence of SEQ ID NO: 6;
  c. binds to human APRIL with about the same $K_D$ as an antibody having a heavy chain comprising the amino acid sequence of SEQ ID NO: 7 and a light chain comprising the amino acid sequence of SEQ ID NO: 8;
  d. blocks binding of human TACI and/or human BCMA to human APRIL with an $IC_{50}$ of about 2 nM or lower.

10. The binding compound of any of the above paragraphs, wherein the binding compound is:
  a. a chimeric antibody or a fragment thereof;
  b. a human antibody or a fragment thereof;
  c. a humanized antibody or a fragment thereof; or
  d. an antibody fragment selected from the group consisting of Fab, Fab', Fab'-SH, Fv, scFv, F(ab')$_2$, bispecific mAb and a diabody.

11. The binding compound of any of the above paragraphs, wherein the binding compound inhibits the proliferation and survival of B-cells.

12. An isolated polynucleotide encoding the binding compound of any one of paragraphs 1 to 11.

13. An expression vector comprising the isolated polynucleotide of paragraph 12.

14. A host cell comprising the expression vector of paragraph 13.

15. A method of producing a binding compound according to any one of paragraphs 1 to 11 comprising:
  a. culturing the host cell of paragraph 14 in culture medium under conditions wherein the polynucleotide is expressed, thereby producing polypeptides comprising the light and heavy chain variable regions; and
  b. recovering the polypeptides from the host cell or culture medium.

16. A composition comprising the binding compound of any one of paragraphs 1 to 11 in combination with a pharmaceutically acceptable carrier or diluent.

17. Binding compound of any one of paragraphs 1 to 11 for use in therapy.

18. The use of the binding compound of any one of paragraphs 1 to 11 for
  a. inhibition of immune cell proliferation and/or survival;
  b. treatment of cancer;
  c. treatment of an autoimmune disease; or
  d. treatment of an inflammatory disease.

19. The use of the binding compound of any one of paragraphs 1 to 11 in a diagnostic method.

The invention claimed is:

1. An isolated antibody or antibody fragment which binds to human A PRoliferating Inducing Ligand (APRIL) comprising:
   a. an antibody heavy chain variable region comprising CDRs SEQ ID NOs: 15, 16 and 17; and
   b. an antibody light chain variable region comprising CDRs SEQ ID NOs: 18, 19 and 20.

2. The isolated antibody or antibody fragment of claim 1 a heavy chain variable region comprising the amino acid sequence of SEQ ID NO: 7 and a light chain variable region comprising the amino acid sequence of SEQ ID NO: 8.

3. The isolated antibody or antibody fragment of claim 1 or 2, wherein the binding compound:
   a. binds human APRIL with a $K_D$ of or about $10^{-8}$ to $10^{-11}$ M; and
   b. blocks binding of human transmembrane activator and calcium modulator and cyclophilin ligand interactor (TACI) to human APRIL with an $IC_{50}$ of about 2 nM or lower.

4. An isolated antibody or antibody fragment which binds to human APRIL wherein the isolated antibody or antibody fragment binds to an epitope having the amino acid sequence of SEQ ID NO: 38 or EGQ.

5. An isolated antibody or antibody fragment which competes for a binding epitope on human APRIL with the binding compound of claim 2, and:
   a. binds human APRIL with a $K_D$ of or about $10^{-8}$ to $10^{-11}$ M;
   b. binds to human APRIL with about the same $K_D$ as an antibody having a heavy chain comprising the amino acid sequence of SEQ ID NO: 7 and a light chain comprising the amino acid sequence of SEQ ID NO: 8; or
   c. blocks binding of human TACI to human APRIL with an $IC_{50}$ of about 2 nM or lower.

6. The isolated antibody or antibody fragment of claim 1, 4 or 5, wherein the isolated antibody or antibody fragment is:
   a. a chimeric antibody or a an antigen-binding fragment thereof;
   b. a human antibody or a an antigen-binding fragment thereof;
   c. a humanized antibody or a an antigen-binding fragment thereof; or
   d. an antibody fragment selected from the group consisting of Fab, Fab', Fab'-SH, Fv, scFv, F(ab')$_2$, bispecific mAb and a diabody.

7. The isolated antibody or antibody fragment of claim 1, 4 or 5, wherein the isolated antibody or antibody fragment inhibits the proliferation and survival of B-cells.

8. A composition comprising the isolated antibody or antibody fragment of claim 1, 4 or 5 in combination with a pharmaceutically acceptable carrier or diluent.

9. A method for treating an APRIL-dependent condition comprising administering an effective amount of the isolated antibody or antibody fragment of claim 1, 4 or 5 wherein the APRIL-dependent condition is selected from the group consisting of APRIL-dependent cancers, APRIL-dependent inflammatory diseases or APRIL-dependent auto-immunity.

10. The method of claim 9, wherein the APRIL-dependent cancer is a B cell malignancy, a Non-Hodgkin's lymphoma and diffuse large B cell lymphoma, or an APRIL-dependent solid tumor.

11. The method of claim 9, wherein the cancer is selected from the group consisting of Chronic Lymphocytic Leukemia (CLL), Multiple Myeloma, Hodgkin's lymphoma, Burkitt's lymphoma, diffuse large B cell lymphoma and a glioblastoma.

12. The method of claim 9, wherein the inflammatory disease is selected from the group consisting of Rheumatoid Arthritis (RA), Systemic Lupus Erythematosus (SLE) and Sjogren's syndrome or Multiple Sclerosis.

13. A method for inhibiting immune cell proliferation and/or survival administrating an effective amount of the isolated antibody or antibody fragment of claim 1, 4 or 5.

14. A diagnostic assay for detecting expression of human APRIL in a cell, tissue or serum by labeling the isolated antibody or antibody fragment of claim 1, 4 or 5 and detecting binding of the labelled isolated antibody or antibody fragment in the cell, tissue or serum.

* * * * *

SEQUENCE LISTING

<160> NUMBER OF SEQ ID NOS: 39

<210> SEQ ID NO 1
<211> LENGTH: 363
<212> TYPE: DNA
<213> ORGANISM: Mus musculus

<400> SEQUENCE: 1
gaggtccagt tgcagcagtc tggacctgag ctggtaaagc ctggggcttc agtgaagatg      60
tcctgcaagg cttctggata cacattcact agctatgtga tgcactgggt gaagcagaag     120
cctgggcagg gccttgagtg gattggatat attaatcctt ataatgatgc tcctaaatac     180
aatgagaagt tcaaaggcaa ggccacagtg acttcagaca gtcctccgg cacagcctac      240 atggagctca gcagcctgac ctctgaggac tctgcggtct attactgtgc aaggggcttg     300
ggttacgccc tttactatgc tatggactac tggggtcaag gaacctcagt caccgtctcc     360
tca                                                                   363

<210> SEQ ID NO 2
<211> LENGTH: 321
<212> TYPE: DNA
<213> ORGANISM: Mus musculus

<400> SEQUENCE: 2
gacattgtga tgacccagtc tcaaaaattc aagtccacat cagtaggaga cagggtcagc      60
gtcacctgca aggccagtca gaatgtgggt aataatgtag cctggtatca acagaaagca     120
gggcaatctc ctaaagcact gatttcctcg gcatccaacc gtgacagtgg agtccctgat     180
cgcttcacag gcagtggatc tgggacagat ttcactctca ccatcagcaa tgtgcagtct     240
gaagacttgg cagactattt ctgtcagcaa tataacatct atccattcac gttcggctcg     300
gggacaaagt tggaaataaa a                                               321

<210> SEQ ID NO 3
<211> LENGTH: 366
<212> TYPE: DNA
<213> ORGANISM: Mus musculus

<400> SEQUENCE: 3
caggttactc tgaaagagtc tggccctggg atattgcagc cctcccagac cctcagtctg      60
acttgttctt tctctgggtt ttcactgagc acttatggta taggagtagg ctggattcgt     120
cagccttcag ggaagggtct ggagtggctg gcacacattt ggtggaatga taataagtac     180
tataacacag ccctgaagag ccggctcaca atctccaagg atacctccaa caaccaggta     240
ttcctcaaga tcgccagtgt ggacactgca gatactgcca catactactg tgctcgaata     300
gctgggggta actacgacta tgctatggac cactggggtc aaggaacctc agtcaccgtc     360
tcctca                                                                366

<210> SEQ ID NO 4
<211> LENGTH: 324
<212> TYPE: DNA
<213> ORGANISM: Mus musculus

<400> SEQUENCE: 4
caaattgttc tcacccagtc tccagcaatc atgtctacat ctcctgggga gaaggtcacc      60
ttgacctgca gtgccagctc aagtgtaagt tctacctact gtactggta ccagcagaag      120 ccaggatcct cccccaaact ctggatttat agcacatcca acctggcttc tggagtccct     180

```
gctcgcttca gtggcagtgg gtctgggacc tcttactctc tcacaatcag cagcatggag    240
gctgaggatg ctgcctctta tttctgccat cagtggagta gttacccacc tacgttcggt    300
gctgggacca agctggagct gaaa                                           324
```

<210> SEQ ID NO 5
<211> LENGTH: 121
<212> TYPE: PRT
<213> ORGANISM: Mus musculus

<400> SEQUENCE: 5

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Ala Pro Lys Tyr Asn Glu Lys Phe
    50                  55                  60

Lys Gly Lys Ala Thr Val Thr Ser Asp Lys Ser Ser Gly Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Leu Gly Tyr Ala Leu Tyr Tyr Ala Met Asp Tyr Trp Gly
            100                 105                 110

Gln Gly Thr Ser Val Thr Val Ser Ser
        115                 120
```

<210> SEQ ID NO 6
<211> LENGTH: 107
<212> TYPE: PRT
<213> ORGANISM: Mus musculus

<400> SEQUENCE: 6

```
Asp Ile Val Met Thr Gln Ser Gln Lys Phe Lys Ser Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Ala Gly Gln Ser Pro Lys Ala Leu Ile
        35                  40                  45

Ser Ser Ala Ser Asn Arg Asp Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ile Tyr Pro Phe
                85                  90                  95

Thr Phe Gly Ser Gly Thr Glu Leu Glu Ile Lys
            100                 105
```

<210> SEQ ID NO 7
<211> LENGTH: 122
<212> TYPE: PRT
<213> ORGANISM: Mus musculus

<400> SEQUENCE: 7

```
Gln Val Thr Leu Lys Glu Ser Gly Pro Gly Ile Leu Gln Pro Ser Gln
1               5                   10                  15
```

```
                    Thr Leu Ser Leu Thr Cys Ser Phe Ser Gly Phe Ser Leu Ser Thr Tyr
                                20                  25                  30

Gly Ile Gly Val Gly Trp Ile Arg Gln Pro Ser Gly Lys Gly Leu Glu
                                35                  40                  45

Trp Leu Ala His Ile Trp Trp Asn Asp Asn Lys Tyr Tyr Asn Thr Ala
                     50                  55                  60

Leu Lys Ser Arg Leu Thr Ile Ser Lys Asp Thr Ser Asn Asn Gln Val
                     65                  70                  75                  80

Phe Leu Lys Ile Ala Ser Val Asp Thr Ala Asp Thr Ala Thr Tyr Tyr
                                    85                  90                  95

Cys Ala Arg Ile Ala Gly Gly Asn Tyr Asp Tyr Ala Met Asp His Trp
                                100                 105                 110

Gly Gln Gly Thr Ser Val Thr Val Ser Ser
                                115                 120

<210> SEQ ID NO 8
<211> LENGTH: 108
<212> TYPE: PRT
<213> ORGANISM: Mus musculus

<400> SEQUENCE: 8

Gln Ile Val Leu Thr Gln Ser Pro Ala Ile Met Ser Thr Ser Pro Gly
                    1               5                   10                  15

Glu Lys Val Thr Leu Thr Cys Ser Ala Ser Ser Val Ser Ser Thr
                                20                  25                  30

Tyr Leu Tyr Trp Tyr Gln Gln Lys Pro Gly Ser Ser Pro Lys Leu Trp
                                35                  40                  45

Ile Tyr Ser Thr Ser Asn Leu Ala Ser Gly Val Pro Ala Arg Phe Ser
                     50                  55                  60

Gly Ser Gly Ser Gly Thr Ser Tyr Ser Leu Thr Ile Ser Ser Met Glu
                     65                  70                  75                  80

Ala Glu Asp Ala Ala Ser Tyr Phe Cys His Gln Trp Ser Ser Tyr Pro
                                    85                  90                  95

Pro Thr Phe Gly Ala Gly Thr Lys Leu Glu Leu Lys
                                100                 105

<210> SEQ ID NO 9
<211> LENGTH: 5
<212> TYPE: PRT
<213> ORGANISM: Mus musculus

<400> SEQUENCE: 9

Ser Tyr Val Met His
1               5

<210> SEQ ID NO 10
<211> LENGTH: 17
<212> TYPE: PRT
<213> ORGANISM: Mus musculus

<400> SEQUENCE: 10

Tyr Ile Asn Pro Tyr Asn Asp Ala Pro Lys Tyr Asn Glu Lys Phe Lys
1               5                   10                  15

Gly

<210> SEQ ID NO 11
<211> LENGTH: 12
<212> TYPE: PRT
<213> ORGANISM: Mus musculus
```

-continued

<400> SEQUENCE: 11

Gly Leu Gly Tyr Ala Leu Tyr Tyr Ala Met Asp Tyr
1               5                   10

<210> SEQ ID NO 12
<211> LENGTH: 11
<212> TYPE: PRT
<213> ORGANISM: Mus musculus

<400> SEQUENCE: 12

Lys Ala Ser Gln Asn Val Gly Asn Asn Val Ala
1               5                   10

<210> SEQ ID NO 13
<211> LENGTH: 7
<212> TYPE: PRT
<213> ORGANISM: Mus musculus

<400> SEQUENCE: 13

Ser Ala Ser Asn Arg Asp Ser
1               5

<210> SEQ ID NO 14
<211> LENGTH: 9
<212> TYPE: PRT
<213> ORGANISM: Mus musculus

<400> SEQUENCE: 14

Gln Gln Tyr Asn Ile Tyr Pro Phe Thr
1               5

<210> SEQ ID NO 15
<211> LENGTH: 7
<212> TYPE: PRT
<213> ORGANISM: Mus musculus

<400> SEQUENCE: 15

Thr Tyr Gly Ile Gly Val Gly
1               5

<210> SEQ ID NO 16
<211> LENGTH: 16
<212> TYPE: PRT
<213> ORGANISM: Mus musculus

<400> SEQUENCE: 16

His Ile Trp Trp Asn Asp Asn Lys Tyr Tyr Asn Thr Ala Leu Lys Ser
1               5                   10                  15

<210> SEQ ID NO 17
<211> LENGTH: 12
<212> TYPE: PRT
<213> ORGANISM: Mus musculus

<400> SEQUENCE: 17

Ile Ala Gly Gly Asn Tyr Asp Tyr Ala Met Asp His
1               5                   10

<210> SEQ ID NO 18
<211> LENGTH: 12
<212> TYPE: PRT
<213> ORGANISM: Mus musculus

<400> SEQUENCE: 18

```
Ser Ala Ser Ser Val Ser Thr Tyr Leu Tyr
1               5                   10
```

<210> SEQ ID NO 19
<211> LENGTH: 7
<212> TYPE: PRT
<213> ORGANISM: Mus musculus

<400> SEQUENCE: 19

```
Ser Thr Ser Asn Leu Ala Ser
1               5
```

<210> SEQ ID NO 20
<211> LENGTH: 9
<212> TYPE: PRT
<213> ORGANISM: Mus musculus

<400> SEQUENCE: 20

```
His Gln Trp Ser Ser Tyr Pro Pro Thr
1               5
```

<210> SEQ ID NO 21
<211> LENGTH: 147
<212> TYPE: PRT
<213> ORGANISM: Homo sapiens

<400> SEQUENCE: 21

```
Arg Ala Val Leu Thr Gln Lys Gln Lys Gln His Ser Val Leu His
1               5                   10                  15

Leu Val Pro Ile Asn Ala Thr Ser Lys Asp Asp Ser Asp Val Thr Glu
            20                  25                  30

Val Met Trp Gln Pro Ala Leu Arg Arg Gly Arg Gly Leu Gln Ala Gln
        35                  40                  45

Gly Tyr Gly Val Arg Ile Gln Asp Ala Gly Val Tyr Leu Leu Tyr Ser
    50                  55                  60

Gln Val Leu Phe Gln Asp Val Thr Phe Thr Met Gly Gln Val Val Ser
65                  70                  75                  80

Arg Glu Gly Gln Gly Arg Gln Glu Thr Leu Phe Arg Cys Ile Arg Ser
                85                  90                  95

Met Pro Ser His Pro Asp Arg Ala Tyr Asn Ser Cys Tyr Ser Ala Gly
            100                 105                 110

Val Phe His Leu His Gln Gly Asp Ile Leu Ser Val Ile Ile Pro Arg
        115                 120                 125

Ala Arg Ala Lys Leu Asn Leu Ser Pro His Gly Thr Phe Leu Gly Phe
    130                 135                 140

Val Lys Leu
145
```

<210> SEQ ID NO 22
<211> LENGTH: 10
<212> TYPE: PRT
<213> ORGANISM: Homo sapiens

<400> SEQUENCE: 22

```
Gln Lys Lys Gln His Ser Val Leu His Leu
1               5                   10
```

<210> SEQ ID NO 23
<211> LENGTH: 8
<212> TYPE: PRT

<213> ORGANISM: Homo sapiens

<400> SEQUENCE: 23

Ala Leu Arg Arg Gly Arg Gly Leu
1               5

<210> SEQ ID NO 24
<211> LENGTH: 9
<212> TYPE: PRT
<213> ORGANISM: Homo sapiens

<400> SEQUENCE: 24

Gln Ala Gln Gly Tyr Gly Val Arg Ile
1               5

<210> SEQ ID NO 25
<211> LENGTH: 8
<212> TYPE: PRT
<213> ORGANISM: Homo sapiens

<400> SEQUENCE: 25

Gln Asp Ala Gly Val Tyr Leu Leu
1               5

<210> SEQ ID NO 26
<211> LENGTH: 11
<212> TYPE: PRT
<213> ORGANISM: Homo sapiens

<400> SEQUENCE: 26

Ser Arg Glu Gly Gln Gly Arg Gln Glu Thr Val
1               5                   10

<210> SEQ ID NO 27
<211> LENGTH: 11
<212> TYPE: PRT
<213> ORGANISM: Homo sapiens

<400> SEQUENCE: 27

Phe His Leu His Gln Gly Asp Ile Leu Ser Val
1               5                   10

<210> SEQ ID NO 28
<211> LENGTH: 13
<212> TYPE: PRT
<213> ORGANISM: Homo sapiens

<400> SEQUENCE: 28

Ile Asn Ala Thr Ser Lys Asp Ser Asp Val Thr Glu
1               5                   10

<210> SEQ ID NO 29
<211> LENGTH: 11
<212> TYPE: PRT
<213> ORGANISM: Homo sapiens

<400> SEQUENCE: 29

Val Leu Phe Gln Asp Val Thr Phe Thr Met Gly
1               5                   10

<210> SEQ ID NO 30
<211> LENGTH: 15
<212> TYPE: PRT
<213> ORGANISM: Homo sapiens

```
<400> SEQUENCE: 30

Ile Arg Ser Met Pro Ser His Pro Asp Arg Ala Tyr Asn Ser Cys
 1               5                  10                  15

<210> SEQ ID NO 31
<211> LENGTH: 9
<212> TYPE: PRT
<213> ORGANISM: Homo sapiens

<400> SEQUENCE: 31

Ile Ile Pro Arg Ala Arg Ala Lys Leu
 1               5

<210> SEQ ID NO 32
<211> LENGTH: 11
<212> TYPE: PRT
<213> ORGANISM: Homo sapiens

<400> SEQUENCE: 32

Asn Leu Ser Pro His Gly Thr Phe Leu Gly Phe
 1               5                  10

<210> SEQ ID NO 33
<211> LENGTH: 11
<212> TYPE: PRT
<213> ORGANISM: Homo sapiens

<400> SEQUENCE: 33

Ile Arg Ser Met Pro Ser His Pro Asp Arg Ala
 1               5                  10

<210> SEQ ID NO 34
<211> LENGTH: 6
<212> TYPE: PRT
<213> ORGANISM: Homo sapiens

<400> SEQUENCE: 34

Ser Met Pro Ser His Pro
 1               5

<210> SEQ ID NO 35
<211> LENGTH: 4
<212> TYPE: PRT
<213> ORGANISM: Homo sapiens

<400> SEQUENCE: 35

Thr Leu Phe Arg
 1

<210> SEQ ID NO 36
<211> LENGTH: 9
<212> TYPE: PRT
<213> ORGANISM: Homo sapiens

<400> SEQUENCE: 36

Gln Asp Val Thr Phe Thr Met Gly Gln
 1               5

<210> SEQ ID NO 37
<211> LENGTH: 5
<212> TYPE: PRT
<213> ORGANISM: Homo sapiens

<400> SEQUENCE: 37
```

```
Val Thr Phe Thr Met
1               5

<210> SEQ ID NO 38
<211> LENGTH: 9
<212> TYPE: PRT
<213> ORGANISM: Homo sapiens

<400> SEQUENCE: 38

Val Ser Arg Glu Gly Gln Gly Arg Gln
1               5

<210> SEQ ID NO 39
<211> LENGTH: 6
<212> TYPE: PRT
<213> ORGANISM: Homo sapiens

<400> SEQUENCE: 39

Thr Phe Thr Met Gly Gln
1               5
```